US006787359B1

(12) United States Patent
Ueno et al.

(10) Patent No.: US 6,787,359 B1
(45) Date of Patent: Sep. 7, 2004

(54) GENE TRANSFER METHODS

(75) Inventors: Mitsuhiro Ueno, Kusatsu (JP); Hirofumi Yoshioka, Kusatsu (JP); Haruko Konishi, Kyoto (JP); Kimikazu Hashino, Takatsuki (JP); Mio Morishita, Otsu (JP); Hideto Chono, Moriyama (JP); Tsuyoshi Miyamura, Kusatsu (JP); Mutsumi Sano, Otsu (JP); Kiyozo Asada, Shiga (JP); Kei Fujinaga, Otsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/743,354

(22) PCT Filed: Jun. 25, 1999

(86) PCT No.: PCT/JP99/03403

§ 371 (c)(1),
(2), (4) Date: Jan. 9, 2001

(87) PCT Pub. No.: WO00/01836

PCT Pub. Date: Jan. 13, 2000

(30) Foreign Application Priority Data

Jul. 1, 1998 (JP) ............................................. 10-186240
Mar. 4, 1999 (JP) ............................................. 11-056915

(51) Int. Cl.[7] ......................... C12N 15/63; C12N 15/87
(52) U.S. Cl. ................... 435/456; 435/455; 435/320.1; 435/5; 435/6; 435/7.1; 435/7.2; 435/325; 435/366; 435/395
(58) Field of Search ................................ 435/455, 456, 435/320.1, 5, 6, 7.1, 7.2, 325, 366, 395

(56) References Cited

U.S. PATENT DOCUMENTS

| 5,656,456 | A | | 8/1997 | Stout et al. |
| 6,013,628 | A | * | 1/2000 | Skubitz et al. ................. 514/12 |
| 6,146,885 | A | * | 11/2000 | Dornburg ................. 435/320.1 |
| 6,426,042 | B1 | * | 7/2002 | Asada et al. .................... 422/61 |
| 6,472,204 | B1 | * | 10/2002 | Asada et al. ............. 435/320.1 |
| 6,472,212 | B1 | * | 10/2002 | Valerio et al. ............... 435/456 |

FOREIGN PATENT DOCUMENTS

| EP | 0 531 733 | 3/1993 |
| EP | 0 844 004 | 5/1998 |
| EP | 0 870 839 | 10/1998 |
| JP | 8-317785 | 3/1996 |
| WO | WO 92/00524 | 1/1992 |
| WO | 95 26200 | 10/1995 |
| WO | WO 97/11604 A1 | 4/1997 |
| WO | WO 97/18318 | 5/1997 |

OTHER PUBLICATIONS

Olsen et al., Human Gene Therapy, 1995, vol. 6, pp. 1195–1202.*

W–Z Ho et al; "Centrifugal Enhancement of Human Immunodeficiency Virus Type I Infection and Human Cytomegalovirus Gene Expression in Human Primary Monocyte/Macrophages in Vitro"; *Journal of Leukocyte Biology*, Federation of American Societies for Experimental; vol. 53, No. 2, Feb. 1993; pp. 208–212.

J.C. Pages et al; Activation of Moloney Murine Leukemia Virus LTR Enhances the Titer of Recombinant Retrovirus in psi–CRIP Packaging Cells; *Gene Therapy*; vol. 2, No. 8, Oct. 1995; pp. 547, 551.

C. Sappey et al; Iron Chelation Decreases NF–kB and HIV type I Activation Due to Oxidative Stress; *Aids Research and Human Retroviruses*; vol. 11, No. 9, 1995, pp. 1049–1061.

Ho et al., "Centrifugal enhancement of human immunodeficiency virus type 1 infection an human cytomegalovirus gene expression in human primary monocyte/macrophages in virtro", (1993), *Journal of Leukocyte Biology*, vol. 53, pp. 208–212.

Moritz et al., "Fibronectin Improves Transduction of Reconstituting Hematopoietic Stem Cells by Retroviral Vectors: Evidence of Direct Viral Binding to Chymotryptic Carboxy–Terminal Fragments", *Blood*, vol. 88, No. 3, pp. 855–862, (1996).

Moritz et al., "Bone Marrow Extracellular Matrix Molecules Improves Gene Transfer into Human Hematopoietic Cells via Retroviral Vectors", *J. Clin. Invest*, vol. 93, pp. 1451–1457, (1994).

Chu et al., "Retroviral Vector Particles Displaying the Antigen–Binding Site of an Antibody Enable Cell–Type–Specific Gene Transfer", *Journal of Virology*, vol. 69, No. 4, pp. 2659–2663, (1995).

* cited by examiner

*Primary Examiner*—David Guzo
(74) *Attorney, Agent, or Firm*—Browdy and Neimark, P.L.L.C.

(57) ABSTRACT

Improved methods for transferring a gene into target cells by using a retrovirus, wherein the gene transfer efficiency is improved and the target cells are efficiently transformed by binding the retrovirus to a functional substance which is immobilized on as carrier and having an activity of binding to retroviruses followed by washing; using an antibody capable of specifically recognizing cells, laminin or mannose-rich type sugar chain as a substance having an activity of binding to the target cells; pre-treating the target cells so as to inactivate transferrin receptor, or introducing a new functional group into the functional substance.

26 Claims, 5 Drawing Sheets

GENE TRANSFER METHODS

The present application is the national stage under 35 U.S.C. 371 of PCT/JP99/03403, filed Jun. 25, 1999.

TECHNICAL FIELD

The present invention relates to a method that increases the efficiency of gene transfer into target cells and enables efficient transduction of the target cells, as well as a series of related techniques therewith, in the fields of medicine, cell technology, genetic engineering, developmental technology and the like.

BACKGROUND ART

Mechanisms of a number of human diseases have been elucidated. The recombinant DNA techniques and the techniques for transferring a gene into cells have rapidly progressed. Under these circumstances, protocols for somatic gene therapies for treating severe genetic diseases have been recently developed. More recently, attempts have been made to apply the gene therapy not only to treatment of the genetic diseases but also to treatment of viral infections such as AIDS and cancers.

In most of the gene therapies which have been examined for clinical application to humans to date, a gene is transferred into cells by using a recombinant retrovirus vector. The retrovirus vector efficiently transfers the foreign gene of interest into cells and stably integrates the gene into their chromosomal DNA. Therefore, it is a preferable means of gene transfer particularly for the gene therapy in which a long-term gene expression is desired. Such a vector has been subjected to various modifications so as not to have a harmful influence on the organism with the transferred gene. For example, the replication function of the vector is eliminated such that the vector used for the gene transfer does not replicate in the cells while repeating unlimited infection (gene transfer).

Since such a vector (a replication-deficient retrovirus vector) cannot autonomously replicate, a retrovirus vector encapsidated in a virus particle is generally prepared by using retrovirus-producer cells (packaging cells). The simplest method for efficiently transferring a gene into target cells comprises co-culturing the target cells with the retrovirus-producer cells. However, the retrovirus-producer cells may be contaminated in the gene transferred target cells which will be transplanted to a living body in this method.

Recently, it was reported that the presence of fibronectin, a component of the extracellular matrix, or a fragment thereof increases the efficiency of gene transfer into cells using a retrovirus (J. Clin. Invest., 93:1451–1457 (1994); Blood, 88:855–862 (1996)). Also, it has been demonstrated that a fibronectin fragment produced by genetic engineering technique has similar properties and can be utilized to efficiently transfer a foreign gene into hematopoietic stem cells (WO 95/26200). It is suggested that the binding of a heparin-binding region in fibronectin to a retrovirus is involved in the increase in gene transfer efficiency due to fibronectin.

Furthermore, it is disclosed in WO 97/18318 that functional substances other than fibronectin such as fibroblast growth factor increase the gene transfer efficiency. The publication also discloses that similar increase in the gene transfer efficiency is also observed when a mixture of a functional substance having an activity of binding to a retrovirus and another functional substance having an activity of binding to cells is used.

The gene transfer methods using functional substances enable an efficient gene transfer without co-cultivating retrovirus-producer cells and target cells. It is believed that the increase in gene transfer efficiency by the methods is due to the increase in chance of interaction between the retrovirus and the target cells which are closely co-localized with the aid of the functional substances.

In gene transfer using a retrovirus, target cells are infected with the retrovirus, resulting in gene transfer as described above. However, the gene transfer efficiency using a retrovirus is still unsatisfactory for practical clinical application. Thus, it is desired to further increase the infection efficiency.

Increased infection efficiency or gene transfer efficiency may be accomplished by increasing the concentration (titer) of the retrovirus in the virus suspension (supernatant) used. However, construction and establishment of virus-producer cells that can produce high titer viruses usually requires much labor. A pseudo-type virus vector utilizing an envelope protein from vesicular stomatitis virus [Proc. Natl. Acad. Sci. USA, 90:8033–8037 (1993)] can be concentrated by centrifugation. However, since such concentration can be used only for this vector, it can not be widely used.

Additionally, specific infection of target cells with a retrovirus in gene transfer may accomplish high gene transfer efficiency even if the purity of target cells is low. However, no convenient and efficient method is known in the current state of the art.

OBJECTS OF INVENTION

In view of the circumstances as described above, the main object of the present invention is to provide an improved method for transferring a gene into target cells using a retrovirus, in which the gene transfer efficiency is increased and the target cells are efficiently transduced.

Hereinafter, other objects and advantages of the present invention will be explained in detail with reference to the attached drawings.

SUMMARY OF INVENTION

Figure 1:
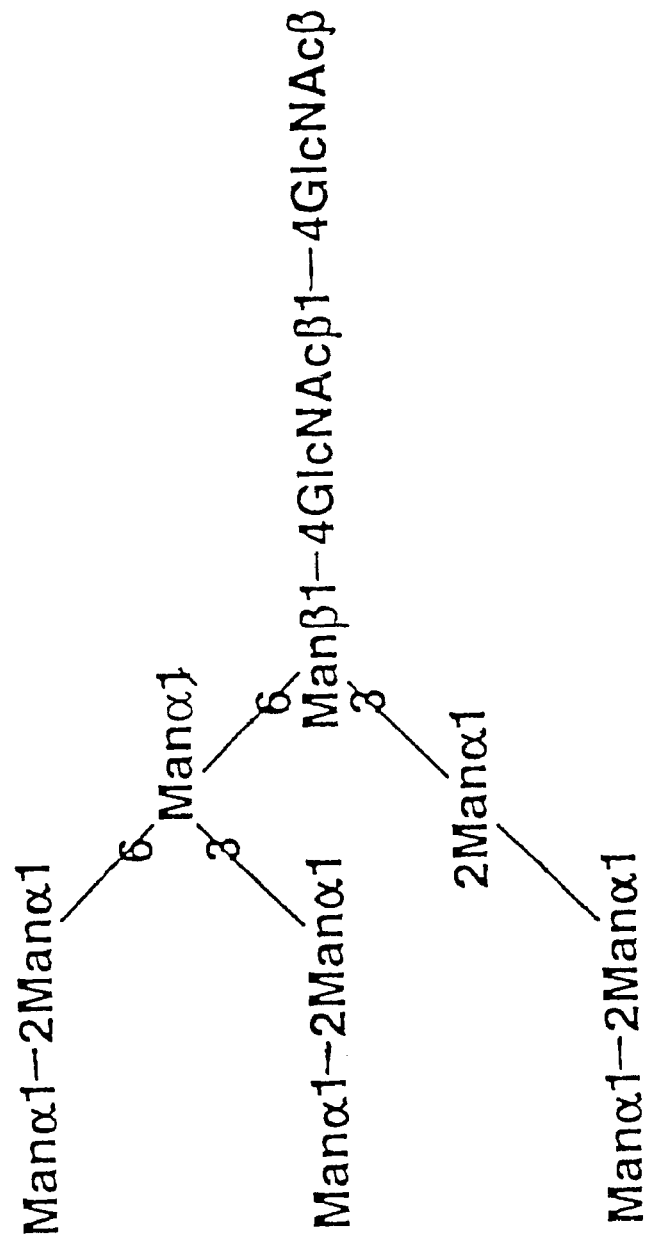
FIG. 1 illustrates a structure of a high mannose type sugar chain containing nine mannose residues in the molecule.

The present inventors have found that gene transfer efficiency is increased by contacting a functional substance having an activity of binding to a retrovirus and being immobilized on a substrate with a retrovirus and then washing the substrate prior to infecting the target cells.

The present inventors have also found that a gene can be transferred specifically for target cells of interest and/or efficiently by infecting the target cells with a retrovirus in the presence of a functional substance such as an antibody which specifically binds to the target cells, laminin, a sugar chain derived from laminin or a high mannose type sugar chain.

The present inventors have further found that gene transfer efficiency can be increased by appropriately pre-treating target cells before subjecting them to gene transfer.

Furthermore, the present inventors have found that the effect on gene transfer of a functional substance having an activity of binding to a virus can be improved by chemically modifying the substance to increase its basicity.

The present invention is completed based on these new findings by the present inventors.

Thus, the first aspect of the present invention is a method for transferring a gene into target cells using a retrovirus, characterized in that the method comprises:

(1) contacting a solution containing a retrovirus with a functional substance having an activity of binding to the retrovirus and being immobilized on a substrate;

(2) washing the substrate to which the retrovirus is bound; and (3) contacting and incubating the substrate to which the retrovirus is bound with target cells.

Without limitation, step (1) above is carried out, for example, for 1 hour or longer, preferably for 3 hours or longer. In addition, the frequency of contact between the retrovirus and the functional substance having an activity of binding to the retrovirus may be physically increased.

Examples of the functional substances having an activity of binding to the retrovirus which can be used in the present invention include, but are not limited to, fibronectin, fibroblast growth factor, collagen type V, polylysine and DEAE-dextran, as well as fragments thereof and substances having an equivalent activity of binding to the retrovirus thereto. The functional substance may have an activity of binding to target cells. Alternatively, the functional substance may be used in combination with another functional substance having an activity of binding to the target cells. Examples of the functional substances having an activity of binding to the target cells which can be used include, but are not limited to, cell-adhesive proteins, hormones, cytokines, antibodies, sugar chains, carbohydrates and metabolites.

For example, a culture supernatant of retrovirus-producer cells can be used as a retrovirus for gene transfer in the present invention. The culture supernatant may be obtained in the presence of a substance that enhances retrovirus production such as sodium butyrate.

The second aspect of the present invention is a method for transferring a gene into target cells using a retrovirus, characterized in that the method comprises infecting target cells with a retrovirus in the presence of two functional substances:

(1) a functional substance having an activity of binding to the retrovirus; and (2) an antibody which specifically binds to the target cells.

Examples of the antibodies which specifically bind to the target cells used in the present invention include, but are not limited to, one that recognizes a biological substance on the surface of the target cells.

The third aspect of the present invention is a method for transferring a gene into target cells using a retrovirus, characterized in that the method comprises infecting target cells with a retrovirus in the presence of two functional substances:

(1) a functional substance having an activity of binding to the retrovirus; and (2) laminin, a laminin fragment, a sugar chain derived from laminin or a high mannose type sugar chain.

Examples of the functional substances having an activity of binding to the retrovirus which can be used in the second and third aspects of the present invention include, but are not limited to, fibronectin, fibroblast growth factor, collagen type V, polylysine and DEAE-dextran, as well as fragments thereof and substances having an equivalent activity of binding to the retrovirus thereto. The functional substance may have an activity of binding to target cells. Furthermore, the functional substance may be used being immobilized on an appropriate substrate.

The fourth aspect of the present invention is a method for transferring a gene into target cells using a retrovirus, characterized in that the method comprises culturing target cells in a medium that contains Fe at a lowered concentration before the target cells are contacted with the retrovirus. Examples of culture media which can be used in the present invention include, but are not limited to, a medium that contains deferoxamine. Preferably, the method is carried out in the presence of a functional substance.

The fifth aspect of the present invention relates to a method for increasing an activity of binding to a retrovirus of a peptide or a protein, characterized in that the method comprises chemically modifying a peptide or a protein. Examples of the chemical modifications include, but are not limited to, activation of an amino acid residue in the peptide or the protein and introduction of a basic residue. For example, the activation of an amino acid residue is preferably carried out by treating the peptide or the protein with a water-soluble carbodiimide or with a water-soluble carbodiimide and a diamino compound, without limitation. The chemically modified peptide or protein obtained by the method can be preferably used for gene transfer into target cells using a retrovirus.

DETAILED DESCRIPTION OF THE INVENTION

A recombinant retrovirus vector is usually used in the gene transfer method of the present invention. In particular, a replication-deficient recombinant retrovirus vector is preferably used. The ability of replication of such a vector is eliminated such that it cannot autonomously replicate in infected cells and, therefore, the vector is non-pathogenic. The vector can invade into a host cell such as a vertebrate cell (particularly, a mammalian cell) and stably integrate a foreign gene inserted within the vector into the chromosomal DNA.

In the present invention, the foreign gene to be transferred into the cells can be used by inserting it into the recombinant retrovirus vector under the control of an appropriate promoter, for example, the LTR promoter in the retrovirus vector or a foreign promoter. In addition, another regulatory element (e.g., an enhancer sequence or a terminator sequence) which cooperates with the promoter and a transcription initiation site may be present in the vector in order to accomplish efficient transcription of the foreign gene. The foreign gene to be transferred may be a naturally occurring gene or an artificially prepared gene. Alternatively, the foreign gene may be one in which DNA molecules of different origins are joined together by ligation or other means known in the art.

One can select any gene of which the transfer into cells is desired as the foreign gene to be inserted into the retrovirus vector. For example, a gene encoding an enzyme or a protein associated with the disease to be treated, an intracellular antibody (see, for example, WO 94/02610), a growth factor, an antisense nucleic acid, a ribozyme, a false primer (see, for example, WO 90/13641) or the like can be used as the foreign gene.

The retrovirus vector used in the present invention may contain a suitable marker gene that enables the selection of gene transferred cells. For example, a drug-resistance gene that confers resistance to antibiotics on cells or a reporter gene that makes it possible to distinguish the gene transferred cells by detecting the enzymatic activity can be utilized as the marker gene.

The vectors that can be used in the present invention includes, for example, retrovirus vectors such as MFG vector (ATCC No. 68754), α-SGC vector (ATCC No. 68755) and LXSN vector [BioTechniques, 7:980–990 (1989)]. Retrovirus vectors used in Examples hereinbelow including PM5neo vector [Exp. Hematol., 23:630–638 (1995)] contain a neomycin phosphotransferase gene as a marker gene. Thus, cells into which a gene is transferred using the vector can be confirmed based on their resistance to G418 as an index.

These vectors can be prepared as virus particles into which the vectors are packaged by using a known packaging cell line such as PG13 (ATCC CRL-10686), PG13/LNc8 (ATCC CRL-10685), PA317 (ATCC CRL-9078), GP+E-86 (ATCC CRL-9642), GP+envAm12 (ATCC CRL-9641) and φCRIP [Proc. Natl. Acad. Sci. USA, 85:6460–6464 (1988)].

Known media such as Dulbecco's Modified Eagle's Medium and Iscoves Modified Dulbecco's Medium can be used for culturing virus-producer cells which are produced by transferring a retrovirus vector into packaging cells, or for culturing target cells. Such media are commercially available, for example, from Gibco. Various constituents can be added to these media depending on the type of the target cells for the gene transfer or other objects. For example, serum or various cytokines can be added to the media in order to promote or suppress the growth or the differentiation of the target cells. For example, calf serum (CS) or fetal calf serum (FCS) can be used as the serum. The cytokine includes interleukines (IL-3, IL-6 etc.), colony-stimulating factors (G-CSF, GM-CSF etc.), stem cell factor (SCF), erythropoietin and various cell growth factors. Many of these cytokines derived from humans are commercially available. One having the suitable activity for the objects is selected from the cytokines. Optionally, the cytokines may be used in combination.

A sample containing a retrovirus such as a culture supernatant of virus-producer cells is used for the gene transfer method of the present invention. The method for preparing the supernatant is not limited to a specific one. For example, it is known that addition of sodium butyrate during the cultivation of virus-producer cells increases the amount of virus particles produced in the supernatant [Human Gene Therapy, 6:1195–1202 (1995)]. The thus prepared high-titer virus supernatant can be used without problem by using the gene transfer method of the present invention.

The method of the present invention is characterized in that target cells are infected with a retrovirus in the presence of a functional substance having a retrovirus-binding site. Gene transferred cells can be efficiently obtained by infecting cells with a retrovirus in the presence of an effective amount of such a functional substance. Furthermore, viral infection-inhibitory substances in a virus supernatant can be readily removed by using the functional substance. Additionally, co-existence of a functional substance having an activity of binding to target cells enables gene transfer with higher specificity and/or efficiency.

As used herein, an effective amount is an amount effective to result in transduction of target cells through the gene transfer into the target cells using a retrovirus. A suitable amount is selected depending on the functional substance to be used and the type of the target cells. The amount can be determined, for example, by measuring the gene transfer efficiency by the method as described herein. As used herein, activities of binding to target cells include not only an activity of substantially binding to cells but also an activity of keeping in contact with target cells in a solution. The activities can be measured based on the contribution to gene transfer efficiency as described above. In addition, gene transfer efficiency means the efficiency of transduction.

The above-mentioned functional substances can be used being dissolved in a solution or being immobilized on an appropriate substrate. The substrate for immobilizing a functional substance is not limited to a specific one. Usually, a vessel for cell culture or a bead-shaped substrate is used.

When a functional substance having an activity of binding to a virus and being immobilized on a substrate is used, gene transfer efficiency can be further increased by using steps as exemplified below.

First, a liquid sample (e.g., a virus supernatant) containing a retrovirus is contacted with a substrate on which a functional substance having an activity of binding to a retrovirus is immobilized. The substrate is washed. The substrate is then directly contacted with target cells. Alternatively, virus particles eluted from the substrate by an appropriate means are added to target cells. Thus, a gene can be efficiently transferred. The functional substance having an activity of binding to a retrovirus used may have an activity of binding to target cells. Alternatively, a functional substance having an activity of binding to a retrovirus and a functional substance having an activity of binding to target cells may be used in combination.

A step of contacting a liquid sample containing a retrovirus with a substrate on which a functional substance having an activity of binding to the retrovirus is immobilized is conducted, for example, for 1 hour or longer, preferably for three hours or longer, without limitation. Also, other conditions including temperature are not specifically limited. For example, the step can be conducted, for example, at room temperature or 37° C. Low temperature around 4° C. may be used depending on the stability of the virus or the like. The substrate for immobilizing a functional substance may be appropriately selected depending on the objects. If a vessel for cell culture is used, one can start gene transfer steps only by adding target cells. For example, phosphate buffered saline or Hanks' saline, liquid medium used for culturing target cells or the like can be used for washing the substrate.

A retrovirus can be more efficiently bound to a functional substance having an activity of binding to the retrovirus by physically increasing the frequency of contact between the retrovirus and the functional substance. Examples of such physical means include, but are not limited to, utilization of shaking, filtration and centrifugal force. Utilization of centrifugal force is specifically exemplified by a method in which a liquid sample containing a retrovirus is added to a centrifugation tube in which a functional substance having an activity of binding to the retrovirus is immobilized at the bottom and the centrifugation tube is then centrifuged. The retrovirus is precipitated onto the bottom of the centrifugation tune by centrifugal force during centrifugation. Accordingly, the frequency of contact between the retrovirus and the functional substance having an activity of binding to the retrovirus is increased, resulting in increase in the frequency of binding. The above-mentioned method does not put the cells under a physical stress like the method in which viruses are precipitated onto cells by centrifugal force for infection (WO 95/10619). Thus, the method of the present invention results in higher gene transfer efficiency.

Gene transfer can be conducted after removing a substance contained in a sample containing a retrovirus, whose existence is not preferable for gene transfer, by the procedure as described above. For example, substances removed by the method of the present invention include a retroviral infection-inhibitory substance derived from packaging cells contained in a virus supernatant [Human Gene Therapy, 8:1459–1467 (1997); J. Virol., 70:6468–6473 (1996)], substances added during culturing retrovirus-producer cells in order to enhance retrovirus production such as phorbol 12-myristate 13-acetate (TPA) and dexamethasone [Gene Therapy, 2:547–551 (1995)], as well as sodium butyrate as described above.

Examples of functional substances having an activity of binding to a retrovirus which can be used in the present invention include, but are not limited to, heparin-II domain of fibronectin, fibroblast growth factor, collagen type V, polylysine and DEAE-dextran, as well as substances functionally equivalent to these functional substances (e.g., a functional substance having a heparin-binding site). Furthermore, a mixture of the functional substances, a polypeptide containing the functional substance, a polymer of the functional substance, a derivative of the functional substance and the like can be used.

The activity of binding to a virus of the functional substance can be enhanced by chemically modifying it. Examples of the chemical modifications include activation of an amino acid residue in the functional substance used and introduction of a basic residue into the substance. For example, the activity of binding to a retrovirus can be increased by modifying a free carboxyl group in a functional substance consisting of a peptide or a protein with a water-soluble carbodiimide such as 1-ethyl-3-dimethylaminopropylcarbodiimide hydrochloride to activate the carboxyl group. Furthermore, the activity of binding to a retrovirus can be increase by utilizing the thus activated carboxyl group to introduce a basic residue such as an amino group into the functional substance.

Examples of the functional substance having an activity of binding to target cells used in the present invention include, but are not limited to, a substance that has a ligand that binds to the target cells. The ligands include cell-adhesive proteins, hormones or cytokines, antibodies against cell surface antigens, polysaccharides, glycoproteins, glycolipids, sugar chains derived from glycoproteins or glycolipids, and metabolites of the target cells. Furthermore, a polypeptide containing the functional substance, a polymer of the functional substance, a derivative of the functional substance, a functional equivalent of the functional substance or the like can be used.

An antibody that specifically binds to target cells is particularly useful for specifically and efficiently transferring a gene into specific cells. The antibody which can be used in the present invention is not limited to a specific one. An antibody against an antigen expressed on target cells into which a gene is to be transferred can be appropriately selected for use. Such an antibody can be produced according to the known methods. Alternatively, many currently commercially available antibodies can also be used. The antibody may be a polyclonal antibody or a monoclonal antibody as long as it has desired properties such as cell specificity. Additionally, an antibody or a derivative of an antibody modified using known techniques such as a humanized antibody, a Fab fragment or a single-chain antibody can also be used.

Expression of respective leukocyte antigens (also known as CD antigens) on various cells has been studied in detail. Thus, a gene can be transferred into target cells with high specificity by selecting an antibody that recognizes a CD antigen expressed on the target cells of interest and using it in the gene transfer method of the present invention. For example, gene transfer can be directed to helper T cells by using an anti-CD4 antibody, or to hematopoietic stem cells by using an anti-CD34 antibody.

Furthermore, a glycoprotein, laminin, can be used as a functional substance having an activity of binding to target cells to efficiently transfer a gene into various target cells such as hematopoietic cells. The laminin which can be used in the present invention may be derived from mouse or human, or it may be a fragment thereof as long as it has an activity of binding to target cells. As described in examples below, the sugar chain of laminin plays an important role in gene transfer using laminin. Therefore, a sugar chain released from laminin according to a known method can also be used in the method of the present invention. Furthermore, a glycoprotein having a high mannose type N-linked sugar chain like laminin, or a sugar chain released therefrom or chemically synthesized can also be used in the present invention. Additionally, a substance such as a protein or the like having the above-mentioned sugar chain being attached thereto can be used. For example, a functional substance having an activity of binding to a retrovirus and having the sugar chain being attached thereto can be preferably used for gene transfer.

The above-mentioned high mannose type sugar chain is not limited to a specific one as long as it has 1 to 20 mannose residues in the molecule. One having a mannose residue at its non-reducing end is preferably used in the method of the present invention. The sugar chain can be used being attached to another appropriate molecule such as a biological molecule. (e.g., a monosaccharide, an oligosaccharide, a polysaccharide, an amino acid, a peptide, a protein or a lipid) or an artificial substance such as a synthetic macromolecule.

Representative high mannose type sugar chains derived from organisms are exemplified by ones having a structure represented by $(Mannose)_n\text{-}(GlucNAc)_2$ [Protein, Nucleic Acid and Enzyme, 43:2631–2639 (1998)]. For example, $(Mannose)_9\text{-}(GlucNAc)_2$, a sugar chain which has the structure as described above and contains nine mannose residues in the molecule, can be preferably used in the gene transfer method of the present invention, without limitation (the structure of this sugar chain is shown in FIG. 1).

The functional substance as described above can be obtained from naturally occurring substances, prepared artificially (for example, by recombinant DNA techniques or chemical synthesis techniques), or prepared by combining a naturally occurring substance and an artificially prepared substance. In addition, a mixture of a functional substance that has a retrovirus-binding site and another functional substance that has a target cell-binding site can be used for the gene transfer using the functional substances as described in WO 97/18318. Alternatively, a functional substance that has a retrovirus-binding site and a target cell-binding site in a single molecule can be used. Functional substances substantially free of other proteins naturally associated therewith are used. Additionally, the functional substance or a combination of the functional substances can be combined with a medium used for culturing target cells, cell growth factor and the like to produce a kit for gene transfer.

Fibronectin or a fragment thereof used in the method of the present invention can be prepared in a substantially pure form from naturally occurring materials according to methods as described, for example, in J. Biol. Chem., 256:7277 (1981); J. Cell. Biol., 102:449 (1986); or J. Cell. Biol., 105:489 (1987). The fibronectin or the fragment thereof can be prepared using recombinant DNA techniques as described in U.S. Pat. No. 5,198,423. Specifically, a fibronectin fragment containing heparin-II domain, which is a retrovirus-binding site, such as recombinant polypeptides including CH-296, H-271, H-296 and CH-271 used in Examples below as well as the method for obtaining them are described in detail in the publication of the above-mentioned patent. These fragments can be obtained by culturing Escherichia coli strains deposited under accession numbers FERM P-10721 (H-296) (the date of the original deposit: May 12, 1989), FERM BP-2799 (CH-271) (the date of the original deposit: May 12, 1989), FERM BP-2800 (CH-296) (the date of the original deposit: May 12, 1989) and FERM BP-2264 (H-271) (the date of the original deposit: Jan. 30, 1989) at the National Institute of Bioscience and Human-Technology, Agency of Industrial Science and Technology, Ministry of International Trade and Industry, 1-3, Higashi 1-chome, Tsukuba-shi, Ibaraki-ken as described in the publication. In addition, fragments that can be typically derived from these fragments can be prepared by modifying the plasmids harbored in these Escherichia coli strains using known recombinant DNA techniques. Among the fibronectin fragments as described above, H-296 has a polypeptide of binding region to VLA-4, CH-271 has a peptide of binding region to VLA-5, and CH-296 has both of them [Nature Medicine, 2:876–882 (1996)].

Gene transferred cells can be efficiently obtained by infecting target cells with a retrovirus in the presence of the functional substance. The infection with the retrovirus can be carried out according to a conventional method, for example, by incubating at 37° C. in 5% $CO_2$. These conditions and the incubation time may be suitably changed depending on the target cells or the objects.

Target cells are not infected with a retrovirus when they are in $G_0$ phase. Therefore, it is preferable to lead the cells into the cell cycle by pre-stimulating them. For this purpose, the target cells are cultured in the presence of growth factor suitable for the target cells prior to the infection of the cells with the retrovirus. For example, various cytokines such as interleukin-3, interleulin-6 and stem cell factor are used to pre-stimulate bone marrow cells or hematopoietic stem cells for gene transfer.

It is known that receptors on the surface of cells are involved in infection of cells with retroviruses. Basic amino acid transporter and phosphate transporter are known to function as receptors for ecotropic viruses and amphotropic viruses, respectively [Proc. Natl. Acad. Sci. USA, 93:11407–11413 (1996)]. It is possible to make target cells susceptible to viral infection by pre-treating the cells in a medium in which concentrations of basic amino acids or phosphates, or salts or precursors thereof are reduced to activate the expression or metabolic turnover of the transporters.

Surprisingly, the present inventors have found that activation of transferrin receptor, of which the involvement in viral infection was not known, also increases efficiency of retroviral infection or gene transfer efficiency. Transferrin receptor can be activated, without limitation, by treating target cells in a medium containing a limited concentration of Fe. For example, a medium in which Fe is chelated by adding deferoxamine can be used.

Preferably, gene transfer using transferrin activation is also carried out in the presence of the functional substance as described above.

Examples of the cell which can be used as the target for the gene transfer by the method of the present invention include, but are not limited to, stem cells, hematopoietic cells, non-adhesive low-density mononuclear cells, adhesive cells, bone marrow cells, hematopoietic stem cells, peripheral blood stem cells, umbilical cord blood cells, fetal hematopoietic stem cells, embryogenic stem cells, embryonic cells, primordial germ cells, oocytes, oogonia, ova, spermatocytes, sperms, CD34+ cells, c-kit+ cells, pluripotent hematopoietic progenitor cells, unipotent hematopoietic progenitor cells, erythroid precursor cells, lymphoid mother cells, mature blood cells, lymphocytes, B cells, T cells, fibroblasts, neuroblasts, neurocytes, endothelial cells, vascular endothelial cells, hepatocytes, myoblasts, skeletal muscle cells, smooth muscle cells, cancer cells, myeloma cells, leukemia cells, and so on. The method of the present invention is preferably utilized for hematopoietic cells which are available from blood and bone marrow because these cells are relatively easy to obtain and because the techniques for culturing and maintaining them are established. Particularly, if a long-term expression of the transferred gene is intended, blood progenitor cells such as hematopoietic stem cells, CD34-positive cells, c-kit-positive cells and pluripotent hematopoietic progenitor cells are suitable as target cells.

For example, a gene therapy using hematopoietic stem cells as target cells can be carried out by the following procedure.

First, a material containing hematopoietic stem cells such as bone marrow tissue, peripheral blood and umbilical cord blood is collected from a donor. Such a material can be directly used in the gene transfer procedure. However, mononuclear cell fractions containing hematopoietic stem cells are usually prepared by means of density-gradient centrifugation and the like, or hematopoietic stem cells are further purified by utilizing cell surface marker molecules such as CD34 and/or c-kit. The material containing the hematopoietic stem cells is infected with a recombinant retrovirus vector, into which a gene of interest is inserted according to the method of the preset invention, after being pre-stimulated by using a suitable cell growth factor, if necessary. The gene transferred cells thus obtained can be transplanted into a recipient, for example, by intravenous administration. Although the recipient is preferably the donor itself, allogenic transplantation can be carried out. For example, if the umbilical cord blood is used as the material, the allogenic transplantation is carried out.

Some of gene therapies using hematopoietic stem cells as target cells are for complementing a deficient or abnormal gene in a patient (e.g., the gene therapy for ADA deficiency or Gaucher's disease). In addition, a drug resistance gene may be transferred into the hematopoietic stem cells in order to alleviate the damage of hematopoietic cells due to the chemotherapeutic agents used for the treatment of cancer or leukemia, for example.

A tumor vaccination therapy is investigated as a gene therapy for cancer. In such therapy, a gene for a cytokine is transferred into cancer cells, the ability of the cancer cells to proliferate are deprived, and the cells are then returned to the body of the patient to enhance the tumor immunity [Human Gene Therapy, 5:153–164 (1994)]. In addition, attempts are made to treat AIDS using a gene therapy. In this case, the following procedure is considered. In the procedure, a gene encoding a nucleic acid molecule (e.g., an antisense nucleic acid or a ribozyme) which interferes with the replication or the gene expression of HIV (human immunodeficiency virus) is transferred into T cells infected with HIV, the causal agent of AIDS [e.g., J. Virol., 69:4045–4052 (1995)].

As described above in detail, a gene can be transferred with high efficiency and with high specificity for target cells by using the present invention. Furthermore, the method of the present invention does not require a specialized equipment or instrument and is effective for various retrovirus vectors and target cells.

EXAMPLES

The following Examples illustrate the present invention in more detail, but are not to be construed to limit the scope thereof.

Example 1

Preparation of Polypeptides Derived from Fibronectin

A polypeptide derived from human fibronectin, H-271, was prepared from *Escherichia coli* HB101/pHD101 (FERM BP-2264) containing a recombinant plasmid pHD101 which contains a DNA encoding the polypeptide according to the method as described in U.S. Pat. No. 5,198,423.

A polypeptide derived from human fibronectin, H-296, was prepared from *Escherichia coli* HB101/pHD102 (FERM P-10721) containing a recombinant plasmid pHD102 which contains a DNA encoding the polypeptide according to the method as described in the above-mentioned publication.

A polypeptide CH-271 was prepared as follows.

Briefly, *Escherichia coli* HB101/pCH101 (FERM BP-2799) was cultured according to the method as described in the above-mentioned publication. CH-271 was obtained from the culture.

A polypeptide CH-296 was prepared as follows.

Briefly, *Escherichia coli* HB101/pCH102 (FERM BP-2800) was cultured according to the method as described in the above-mentioned publication. CH-296 was obtained from the culture.

A polypeptide C-274 was prepared as follows.

Briefly, *Escherichia coli* JM109/pTF7221 (FERM BP-1915) was cultured according to the method as described in U.S. Pat. No. 5,102,988. C-274 was obtained from the culture.

A polypeptide having an activity of binding to a retrovirus derived from collagen type V, ColV, was prepared according to the method as described in WO 97/18318.

Example 2

Construction of Retrovirus Vector and Preparation of Retrovirus Supernatant A retrovirus plasmid, PM5neo vector, which contains a neomycin phosphotransferase gene [Exp. Hematol., 23:630–638 (1995)] was introduced into GP+E-86 cells (ATCC CRL-9642). The cells were cultured in Dulbecco's Modified Eagle's Medium (DMEM; Bio Whittaker) containing 10% fetal calf serum (FCS; Gibco), 50 units/ml of penicillin and 50 $\mu$g/ml of streptomycin (both from Gibco). All of the DMEMs used in the procedure hereinbelow contained the above-mentioned antibiotics. A supernatant containing PM5neo virus was prepared by adding 4 ml of DMEM containing 10% FCS to a plate (a 10-cm gelatin-coated dish for cell culture, Iwaki Glass) in which the above-mentioned producer cells had been grown to semi-confluence, culturing overnight and then collecting the supernatant. The thus collected culture supernatant was filtrated through a 0.45-micron filter (Millipore) to prepare a virus supernatant stock, which was stored at −80° C. until use.

Virus supernatants were prepared from the following cells according to the procedure as described above. Ecotropic packaging BOSC23 cells [Proc. Natl. Acad. Sci. USA, 90:8392–8396 (1993)], into which a retrovirus plasmid pLEIN (Clontech; which contains a neomycin phosphotransferase gene and an enhanced green fluorescent protein (EGFP) gene) had been introduced; and amphotropic packaging $\phi$CRIP cells [Proc. Natl. Acad. Sci. USA, 85:6460–6464 (1988)]. Hereinafter, a virus prepared from BOSC23 cells is referred to as Eco-EGFP, and a virus prepared from $\phi$CRIP cells is referred to as Ampho-EGFP, respectively.

Furthermore, a virus supernatant was prepared from GP+EnvAm12 cells (ATCC CRL-9641) containing a retrovirus plasmid, TKNeo vector [J. Exp. Med., 178:529–536 (1993)] (which contains a neomycin phosphotransferase gene) according to the procedure as described above. DMEM containing 10% calf serum (CS; Gibco) in place of FCS was used.

The titer of the virus supernatant was measured according to a standard method [J. Virol., 62:1120–1124 (1988)] in which the efficiency of transferring a neomycin phosphotransferase gene into NIH/3T3 cells (ATCC CRL-1658) is used as an index. The number of infectious particles contained in 1 ml of the supernatant (cfu/ml) was calculated. The amount of the virus supernatant to be added in the experiments hereinbelow was determined based on the calculated value, i.e., the titer of the supernatant.

Example 3

Preparation of Functional Substance Having Activity of Binding to Retrovirus and Measurement of Activity Thereof 50 $\mu$l of 80 $\mu$/ml solution of H-271, H-296, C-274, CH-271, CH-296, ColV, human basic fibroblast growth factor (bFGF; Progen), tenascin (Gibco) or epidermal growth factor (EGF; Takara Shuzo), or 50 $\mu$l of 2% bovine serum albumin (BSA, Sigma) was added to each well of a 96-well non-treated microplate for cell culture (Falcon). The plate was allowed to stand at 4° C. overnight and then washed twice with phosphate buffered saline (PBS; Roman Kogyo). Alternatively, after the plate was treated as described above, 0.1 ml of 4 mg/ml solution of 1-ethyl-3-dimethylaminopropylcarbodiimide hydrochloride (Sigma) in sterile pure water was dispensed to each well. The reaction was allowed to proceed at 37° C. for 2 hours. The plate was washed extensively with pure water to prepare a carbodiimide-treated plate. These plates were stored at 4° C. until viral infection experiments were conducted.

$10^4$ mouse leukemia L1210 cells (ATCC CCL-219), which had been grown in RPMI 1640 medium (Bio Whittaker) supplemented with 10% FCS, 50 units/ml penicillin and 50 μg/ml streptomycin, and 50 μl of PM5neo virus supernatant ($10^4$ cfu/ml) were added to the well of the microplate. After the plate was incubated for 24 hours, the medium was changed to the same medium containing G418 (Gibco) at a final concentration of 0.75 mg/ml, and the plate was then incubated for additional 48 hours. G418-resistance cells were assessed according to the method as described in S. Kim et al. [Gene Therapy, 3:1018–1020 (1996)] with a partial modification in which color developed using Premix WST-1 reagent (Takara Shuzo) was measured as absorbance at 450 nm. After incubation, 10 μl/100 μl culture of the WST-1 reagent was added to the well, the plate was incubated at 37° C. for additional 4 hours. Absorbance at 450 nm and 650 nm was then measured using a microplate reader, and the difference (450 nm–650 nm) was calculated. The value obtained using a plate coated with 2% BSA without carbodiimide treatment was defined as background. The results from three rounds of studies are summarized in Table 1.

TABLE 1

|  | Functional substance | Untreated | Treated with carbodiimide |
| --- | --- | --- | --- |
| Experiment 1 | BSA | 0.000 ± 0.011 | Not done |
|  | CH-271 | 2.099 ± 0.010 | 2.814 ± 0.079 |
| Experiment 2 | BSA | 0.000 ± 0.007 | 0.224 ± 0.031 |
|  | H-271 | 0.777 ± 0.016 | 0.994 ± 0.029 |
|  | H-296 | 0.474 ± 0.014 | 0.666 ± 0.021 |
|  | C-274 | −0.068 ± 0.017 | 0.100 ± 0.033 |
|  | CH-271 | 0.382 ± 0.017 | 0.425 ± 0.019 |
|  | CH-296 | 0.363 ± 0.023 | 0.460 ± 0.007 |
|  | ColV | 0.644 ± 0.006 | 0.847 ± 0.033 |
|  | bFGF | 0.425 ± 0.014 | 0.580 ± 0.046 |
|  | Tenascin | 0.060 ± 0.021 | 0.323 ± 0.037 |
|  | EGF | 0.030 ± 0.021 | 0.077 ± 0.038 |

(Mean ± standard deviation)

As shown in Table 1, increase in gene transfer efficiency was observed for known functional substances having an activity of binding to a virus, i.e., H-271, H-296, CH-271, CH-296, ColV and bFGF. Furthermore, appearance of G418-resistant cells increased when C-274, tenascin, EGF and BSA, which do not have an activity of binding to a virus, were used and carbodiimide treatment was carried out.

Next, CH-296 was used as a functional substance to carry out experiments as follows.

0.5 ml of 40 μg/ml CH-296 was added to each well of a 24-well non-treated microplate for cell culture (Falcon). The plate was incubated at 4° C. overnight and then washed with PBS (pH 5.8). 625 μl of 10 mg/ml solution of 1-ethyl-3-dimethylaminopropylcarbodiimide hydrochloride (Sigma) in PBS (pH 5.8) containing ethylenediamine [$NH_2(CH_2)_2NH_2$; Nacalai Tesque], trimethylenediamine [$NH_2(CH_2)_3NH_2$; Nacalai Tesque] or putrescine [$NH_2(CH_2)_4NH_2$; Nacalai Tesque] at a varying concentration was added to each well. The plate was incubated at 37° C. for 2 hours. An amino group was introduced to the carboxyl group in the CH-296 molecule through the mediation of carbodiimide in this procedure. The plate was washed three times with PBS, and then blocked with 2% glycine/PBS followed by 2% BSA/PBS.

GP+E86 cells into which a retrovirus vector plasmid pLEIN had been introduced were cultured in DMEM containing 10% CS. Then, a supernatant was collected from the culture. 0.5 ml of a virus supernatant prepared by diluting the supernatant to make the concentration to $1\times10^5$ cfu/ml was added to each well of the plate. The plate was incubated for 4 hours. $1\times10^4$ NIH/3T3 cells were further added to the well. The plate was incubated for 2 days. After incubation, the cells were collected by using a cell detachment buffer (Bio Whittaker) and washed. EGFP-expressing cells were analyzed by flow cytometry using FACSVantage (Becton Dickinson) at an excitation wavelength of 488 nm and an emission wavelength of 515–545 nm. The binding ability of the virus to the plate was expressed by the efficiency of gene transfer into cells. The results are shown in FIG. 2.

Figure 2:
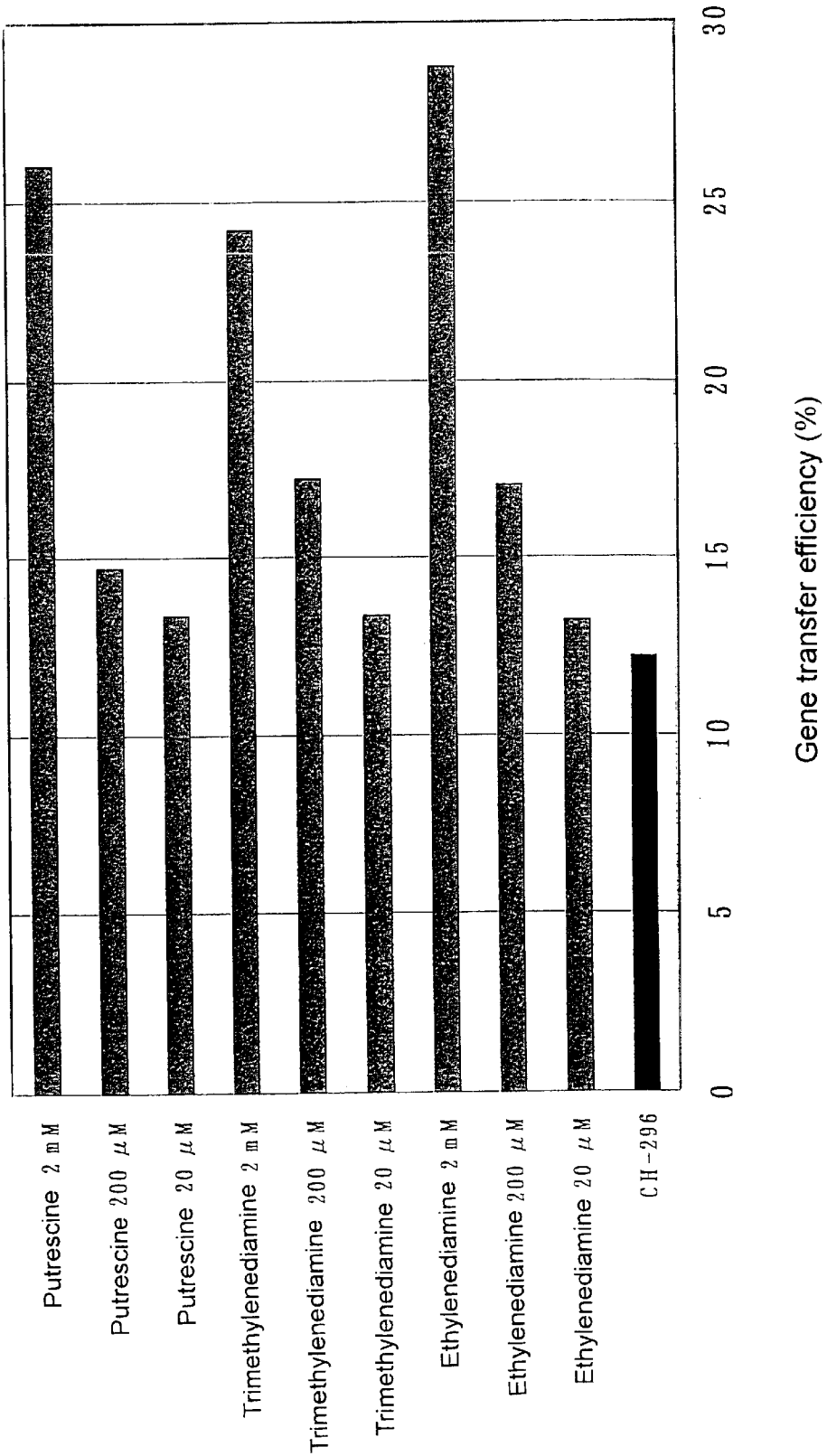
FIG. 2 is a graph that shows the gene transfer efficiency (%) achieved by using chemically modified CH-296 in Example 3.

As shown FIG. 2, the binding ability of the virus increased as the concentration of the diamino compound used for introducing an amino group increased. About two-fold increase in the binding ability of the virus was observed when putrescine, trimethylenediamine or ethylenediamine was used in the reaction at a concentration of 2 mM as compared with the ability observed using untreated CH-296.

Example 4

Effect of Enhancing Gene Transfer Efficiency of Laminin

Mouse laminin (Gibco) or human laminin (Takara Shuzo) was used in combination with a functional substance having an activity of binding to a virus to carry out gene transfer experiment. A 24-well non-treated microplate for cell culture (Falcon) used in the experiment was coated with these functional substances according to the following two methods.

The cocktail method: A mixture of two functional substances is added to the plate. The plate is allowed to stand at 4° C. overnight. The plate is blocked with 2% BSA at 37° C. for 20 minutes and then washed with PBS.

The pre-coating method: A solution of a functional substance having an activity of binding to a virus is added to the plate. The plate is allowed to stand at 4° C. overnight. The solution is removed. A laminin solution is added to the plate. The plate is incubated at 37° C. for 2 hours, blocked with 2% BSA, and then washed with PBS.

0.5 ml of the solution of the functional substance was used to coat each well. $10^5$ L1210 cells and 0.5 ml of Eco-EGFP virus supernatant ($10^5$ cfu/ml) were added to the well. The plate was incubated for 24 hours. After incubation, the cells were collected by using a cell detachment buffer (Bio Whittaker) and washed. EGFP-expressing cells were analyzed by flow cytometry using FACSVantage (Becton Dickinson) at an excitation wavelength of 488 nm and an emission wavelength of 515–545 nm. The gene transfer efficiency (the ratio of EGFP-expressing cells to total cells) was calculated. The experimental results are shown in Tables 2 to 5.

TABLE 2

| | Concentration of laminin added and coating method | | | |
| --- | --- | --- | --- | --- |
| Functional substance (80 μg/ml) | No addition — | 5 μg/ml Pre-coating | 20 μg/ml Pre-coating | 20 μg/ml Cocktail |
| BSA (2%) | 1.12 | 5.20 | 6.55 | 6.22 |
| H-271 | 5.41 | 11.19 | 17.52 | 9.67 |
| H-296 | 4.83 | 5.96 | 5.51 | 6.95 |
| CH-271 | 4.00 | 6.72 | 13.73 | 17.34 |
| CH-296 | 6.48 | 7.08 | 6.02 | 16.77 |

Gene transfer efficiency in % is indicated.

TABLE 3

| Functional substance (80 μg/ml) | Concentration of laminin added | | | |
| --- | --- | --- | --- | --- |
| | No addition | 20 μg/ml | 40 μg/ml | 60 μg/ml |
| BSA (2%) | 1.36 | 5.14 | 4.74 | 3.82 |
| CH-271 | 16.89 | 32.05 | 24.45 | 23.46 |
| CH-296 | 17.80 | 18.79 | 20.44 | 19.31 |

The plate was coated according to the cocktail method.
Gene transfer efficiency in % is indicated.

TABLE 4

| Concentration of CH-296 added | Concentration of laminin added | | | |
| --- | --- | --- | --- | --- |
| | No addition | 5 μg/ml | 10 μg/ml | 20 μg/ml |
| No addition | 0.69 | 4.09 | 6.76 | 6.89 |
| 10 μg/ml | 4.67 | 11.81 | 9.36 | 7.01 |
| 20 μg/ml | 5.16 | 11.64 | 10.57 | 8.49 |
| 40 μg/ml | 4.41 | 10.49 | 11.52 | 9.11 |
| 80 μg/ml | 5.11 | 10.87 | 11.48 | 11.10 |
| 160 μg/ml | 5.19 | 9.04 | 11.84 | 10.88 |
| 320 μg/ml | Not done | Not done | 10.27 | 10.54 |

The plate was coated according to the cocktail method.
Gene transfer efficiency in % is indicated.

TABLE 5

| Concentration of CH-271 added | Concentration of laminin added | | | |
| --- | --- | --- | --- | --- |
| | No addition | 5 μg/ml | 10 μg/ml | 20 μg/ml |
| No addition | 0.69 | 4.09 | 6.76 | 6.89 |
| 10 μg/ml | 4.61 | 7.16 | 6.28 | 6.34 |
| 20 μg/ml | 4.71 | 12.98 | 8.98 | 5.99 |
| 40 μg/ml | 3.64 | 17.32 | 14.50 | 8.78 |
| 80 μg/ml | 3.60 | 18.30 | 14.76 | 9.15 |
| 160 μg/ml | 3.52 | 16.34 | 17.08 | 12.67 |

The plate was coated according to the cocktail method.
Gene transfer efficiency in % is indicated.

As shown in Tables 2 and 3, it was demonstrated that a gene was transferred into target cells very efficiently regardless of the immobilization method when mouse or human laminin was used in combination with a functional substance having an activity of binding to a virus for gene transfer using a retrovirus. The gene transfer efficiency using a plate coated with CH-296 or CH-271 and laminin according to the cocktail method was examined. As shown in Tables 4 and 5, it revealed that the optimal ratios were 8:1 (e.g., 80 μg/ml: 10 μg/ml) for the combination of CH-296/mouse laminin, and 16:1 (e.g., 80 μg/ml: 5 μg/ml) for CH-271/mouse laminin, respectively. The gene transfer efficiency increased 2.6-fold and 5.1-fold for CH-296 and CH-271, respectively, as compared with the efficiency of gene transfer without the addition of laminin.

Example 5

Gene Transfer into Mouse c-kit-positive Bone Marrow Cells Using laminin

Mouse c-kit-positive bone marrow cells were prepared as follows. Bone marrow cells collected from a femur of a 6–8 weeks old C3H/He female mouse (Japan SLC) were subjected to density-gradient centrifugation using Ficoll-Hypaque (1.0875 g/ml, Pharmacia) to prepare a fraction containing low-density mononuclear cells. The cells were washed with PBS, erythrocytes were lysed using Ery-Lysis buffer (155 mM $NH_4Cl$, 10 mM $KHCO_3$, 0.1 mM EDTA, pH 7.4), and the cells were washed again with PBS. 1 μg/$10^7$ cells of an anti-mouse CD117 antibody (Pharmingen) was added to the resulting bone marrow cells. The mixture was reacted on ice for 30 minutes. The cells were washed with PBS containing 5 mM EDTA and 0.5% BSA, and then suspended in the same buffer. 20 μl/$10^7$ cells of a secondary antibody conjugated with a microbead (Miltenyi Biotec) was added to the cells. The mixture was reacted at 4° C. for 30 minutes. The cells were washed with and resuspended in the above-mentioned buffer. Cells bound to the microbeads were collected using MACS system (Miltenyi Biotec) to obtain c-kit-positive cells.

Prior to viral infection, the mouse c-kit-positive bone marrow cells were pre-stimulated in accordance with the method of Luskey et al. [Blood, 80:396–402 (1992)]. Briefly, cells were cultured in α-MEM (Bio Whittaker) containing 20% FCS, 20 ng/ml of recombinant mouse interleukin-3 (Genzyme), 50 ng/ml of recombinant human interleukin-6 (Genzyme), 100 ng/ml of recombinant mouse stem cell factor (Genzyme), 50 units/ml of penicillin and 50 μg/ml of streptomycin 37° C. for 2 days in the presence of 5% $CO_2$.

A 24-well non-treated microplate for cell culture was coated according to the cocktail method using a mixture containing mouse laminin at a varying concentration and 80 μg/ml of CH-271. The plate was blocked with 2% BSA for 30 minutes, and then washed with PBS. A control plate was prepared using 2% BSA in place of CH-271. $10^5$ c-kit-positive bone marrow cells and 0.5 ml Eco-EGFP virus supernatant ($10^5$ cfu/ml) were added to each well of the microplate for viral infection. After incubation for 48 hours, 0.5 ml of fresh medium was added to the well, and the plate was incubated for additional 24 hours. After incubation, the cells were collected by using a cell detachment buffer and washed. The gene transfer efficiency was calculated as described in Example 4. The results from two rounds of experiments are shown in Tables 6 and 7.

TABLE 6

| | Concentration of laminin added | | |
| --- | --- | --- | --- |
| | No addition | 10 μg/ml | 20 μg/ml |
| BSA | 0.18 | 0.25 | 0.16 |
| CH-271 | 0.69 | 3.93 | 2.64 |

Gene transfer efficiency in % is indicated.

TABLE 7

| | Concentration of laminin added | | | |
| --- | --- | --- | --- | --- |
| | No addition | 2.5 μg/ml | 5 μg/ml | 10 μg/ml |
| BSA | 1.37 | 1.80 | 2.63 | 5.38 |
| CH-271 | 9.95 | 16.12 | 15.28 | 17.00 |

Gene transfer efficiency in % is indicated.

As shown in Tables 6 and 7, it was demonstrated that a very strong effect of enhancing gene transfer efficiency was also observed when c-kit-positive bone marrow cells were infected with a retrovirus in a plate coated with mouse laminin and a functional substance having an activity of binding to a virus, CH-271, according to the cocktail method. The efficiency of gene transfer using CH-271 in combination with laminin increase 5.7-fold at the most as compared with that using CH-271 alone.

Furthermore, the same procedure as that described above was carried out using Eco-EGFP virus supernatant at a titer of $10^7$ cfu/ml. The mean gene transfer efficiency from three rounds of experiments is shown in Table 8. It was also demonstrated in this case that the efficiency of gene transfer using a functional substance having an activity of binding to a retrovirus was increased by using laminin in combination.

TABLE 8

| | Concentration of laminin added | | | |
|---|---|---|---|---|
| | No addition | 2 ug/ml | 4 ug/ml | 6 ug/ml |
| BSA | 5.88 | 11.77 | 19.33 | 27.09 |
| H-271 | 25.12 | 53.39 | 55.65 | 56.45 |
| CH-271 | 43.06 | 66.87 | 73.67 | 77.76 |
| CH-296 | 76.84 | 81.57 | 83.30 | 85.48 |

Gene transfer efficiency in % is indicated.

Example 6

Gene Transfer into CD3-Positive T Cells Derived from Mouse Spleen Cells Using Laminin CD3-positive T cells derived from mouse spleen cells were prepared as follows. Cells were collected from a spleen of a 6–8 weeks old C3H/He female mouse. The cells were passed through a 100-μm mesh (Falcon) to remove residuals. The resulting cells were washed with Hanks' balanced salt solution (HBSS, Bio Whittaker) containing 10% FCS, erythrocytes were lysed using Ery-Lysis buffer, and the cells were washed again with HBSS. The resulting cells were passed through a 30-μm mesh (Miltenyi Biotec) to remove residuals and then purified using a column for concentrating CD3-positive T cells (R&D Systems). Mouse CD3-positive T cells used for viral infection experiments were pre-stimulated as follows. The cells were cultured for pre-stimulation in a Petri dish onto which an anti-mouse CD3 antibody and an anti-mouse CD28 antibody (both at 1 μg/ml, Pharmingen) had been immobilized. The Petri dish contained RPMI 1640 medium (Bio Whittaker) supplemented with 10% FCS, 50 units/ml of penicillin and 50 μg/ml of streptomycin. The cells were cultured at 37° C. for 2 days in the presence of 5% $CO_2$.

A 24-well microplate was coated using a mixture containing 20 μg/ml of mouse laminin and 80 μg/ml of CH-296 as described in Example 5. $10^5$ CD3-positive T cells and 0.5 ml Eco-EGFP virus supernatant ($10^5$ cfu/ml) were added to each well of the microplate for viral infection for 3 hours. RPMI 1640 medium containing 10% FCS, 500 units/ml of recombinant mouse interleukin-1α (Genzyme), 10 ng/ml of recombinant mouse interleukin-2 (Genzyme), 50 units/ml of penicillin and 50 μg/ml of streptomycin was added thereto. The incubation was continued for 48 hours. After incubation, the cells were collected by using a cell detachment buffer and washed. The gene transfer efficiency was calculated as described in Example 4. The results are shown in Table 9.

TABLE 9

| Functional substance | Transfer efficiency (%) |
|---|---|
| BSA (control) | 0.83 |
| CH-296 | 8.78 |
| CH-296/mouse laminin | 13.20 |

Gene transfer efficiency in % is indicated.

As shown in Table 9, it was demonstrated that the efficiency of gene transfer into mouse CD3-positive T cells was increased by the co-existence of laminin.

Example 7

Involvement of Sugar Chain of Laminin Molecule in Gene Transfer

A 96-well microplate was coated using 50 μl/well of a mixture containing 5 μg/ml of mouse laminin and 80 μg/ml of CH-271 as described in Example 5. Effects of treatment of the plate with various enzymes having activities of cleaving sugar chains on gene transfer efficiency were examined.

Plates were treated with enzymes as follows: Enzyme solutions containing 500 mU/ml O-glycanase (endo-α-N-acetylgalactosaminidase, Seikagaku Corp.), 500 mU/ml endoglycosidase H (endo-β-N-acetylglucosaminidase H, Seikagaku Corp.), 250 mU/ml endo-β-galactosidase (Seikagaku Corp.) and 2 mU/ml α-mannosidase (Seikagaku Corp.) in 50 mM citrate-phosphate buffer (pH 5.0) were prepared. An enzyme solution containing 250 mU/ml glycopeptidase F (peptide: N-glycosidase F, Takara Shuzo) in 100 mM tris-hydrochloride buffer (pH 8.6) was prepared. 50 μl each of the enzyme solutions was dispensed in each well for reacting at 37° C. for 20 hours. The plate was then washed three times with PBS and then used for viral infection experiments. $10^4$ mouse leukemia L1210 cells grown in RPMI 1640 medium supplemented with 10% FCS, 50 units/ml penicillin and 50 μl/ml streptomycin, and 50 μl of PM5neo virus supernatant ($10^4$ cfu/ml) were added to each well of the microplate. The plate was incubated for 24 hours. The medium was changed to the same medium containing G418 (Gibco) at a final concentration of 0.75 mg/ml. The plate was incubated for additional 48 hours. G418-resistance cells were assessed as described in Example 3. The results are shown in Table 10. Table 10 summarizes results from three rounds of experiments.

TABLE 10

| Functional substance | Enzyme treatment | Absorbance |
|---|---|---|
| BSA (2%, control) | No | 0.000 ± 0.030 |
| CH-271 (80 μg/ml) | No | 1.376 ± 0.012 |
| CH-271/laminin (80 μg/ml: 5 μg/ml) | No | 1.781 ± 0.062 |
| CH-271/laminin (80 μg/ml: 5 μg/ml) | O-Glycanase | 1.886 ± 0.071 |
| CH-271/laminin (80 μg/ml: 5 μg/ml) | Endoglycosidase H | 1.214 ± 0.017 |
| CH-271/laminin (80 μg/ml: 5 μg/ml) | E-β-galactosidase | 1.939 ± 0.083 |
| CH-271/laminin (80 μg/ml: 5 μg/ml) | α-Mannosidase | 1.657 ± 0.033 |
| CH-271/laminin (80 μg/ml: 5 μg/ml) | Glycopeptidase F | 1.610 ± 0.036 |

As shown in Table 10, when CH-271 was used in combination with laminin, the appearance of G418-resistant cells was increased as compared with the case in which CH-271 was used alone. Treatment of the plate coated with laminin with endoglycosidase H completely abolished the gene transfer-promoting effect of laminin. Furthermore, treatment of the plate with α-mannosidase or glycopeptidase F decreased the gene transfer efficiency in some degree. According to a report concerning the sugar chains of a laminin molecule [Biochim. Biophysi. Acta, 883:112–126 (1986)], most of the sugar chains of the laminin molecule are N-linked sugar chains which are bound to asparagine. 43 molecules of N-linked sugar chains are bound to a laminin molecule. Among the sugar chains, high mannose type asparagine-N-linked sugar chains are released by the treatment with endoglycosidase H. The fact that decrease in gene transfer efficiency was also observed when treated with α-mannosidase suggests that sugar chains of the laminin molecule play an important role. Such sugar chains have a structure containing α1-2- and/or α1-6-bonded mannose, which is cleaved with α-mannosidase, represented by (Mannose)$_9$—(GlucNAc)$_2$—Asn and/or (Mannose)$_6$—(GlucNAc)$_2$—Asn. As described above, it was demonstrated that the gene transfer-promoting effect of laminin was due to sugar chains of the laminin molecule, in particular high mannose type sugar chains.

The involvement of (Mannose)$_9$—(GlucNAc)$_2$—Asn in gene transfer was confirmed by the following experiments.

1 g of soybean agglutinin prepared from de-fatted soybean flour (Sigma) using Sepharose CL-2B (Pharmacia) to which lactose had been immobilized was heated-denatured, and then digested with 20 mg of Actinase E (Kaken Pharmaceutical) in 20 ml of 50 mM tris-hydrochloride buffer (pH 7.2) containing 10 mM calcium chloride at 37° C. for 2 days. After heat-inactivating the enzyme, the mixture was subjected to a chromatography using Sephadex G-15 (50 ml) column and Sephadex G-25 (150 ml) column to purify (Mannose)$_9$-(GlucNAc)$_2$-Asn. FIG. 1 illustrates the structure of (Mannose)$_9$-(GlucNAc)$_2$-Asn from which the asparagine residue is removed.

A microplate to which CH-271 and (Mannose)$_9$-(GlucNAc)$_2$-Asn were immobilized through covalent bonds was prepared. Briefly, a 96-well Carboplate (ELISA Carbotype plate) (Sumitomo Bakelite) was activated using 4 mg/ml water-soluble carbodiimide solution at 37° C. for 2 hours, and then washed three times with sterile water. 50 μl each of solutions containing 2% BSA or 80 μg/ml of CH-271 as well as (Mannose)$_9$-(GlucNAc)$_2$-Asn at a varying concentration was added to each well of the activated 96-well Carboplate. The plate was subjected to immobilization reaction at 37° C. for 2 hours. The plate was blocked using 0.2% glycine solution at 4° C. for 15 hours and then used for the following gene transfer experiments.

$10^3$ L1210 cells and 0.1 ml Eco-EGFP virus supernatant ($10^6$ cfu/ml) were added to the well of the microplate. After the plate was incubated for 48 hours, 0.1 ml of fresh RPMI 1640 medium containing FCS, penicillin and streptomycin was added to the well. The plate was incubated for additional 24 hours. The cells were collected and washed. The gene transfer efficiency was calculated as described in Example 4. The mean results from two independent experiments are shown in Table 11.

TABLE 11

| Functional substance (80 μg/ml) | Concentration of sugar chain added | | | | | | |
|---|---|---|---|---|---|---|---|
| | No addition | 2.8 μg/ml | 5.5 μg/ml | 11.1 μg/ml | 22.1 μg/ml | 44.2 μg/ml | 88.5 μg/ml |
| BSA (2%) | 1.68 | Not done | Not done | Not done | 1.24 | 1.65 | Not done |
| CH-271 | 26.9 | 27.1 | 29.9 | 34.7 | 39.2 | 52.0 | 58.7 |

Gene transfer efficiency in % is indicated.

As shown in Table 11, the gene transfer efficiency for the wells on which (Mannose)$_9$-(GlucNAc)$_2$-Asn and CH-271 had been immobilized was increased depending on the concentration of sugar chain used. Thus, it was confirmed that the sugar chain having the same structure as that of the laminin molecule contributed to the increase in gene transfer efficiency.

Example 8

Gene Transfer Specific for CD4-positive Cells Using Anti-CD4 Monoclonal Antibody A 24-well non-treated microplate for cell culture was coated with a combination of 1 μg/ml of an anti-mouse CD4 monoclonal antibody or an anti-mouse CD44 monoclonal antibody (both from Pharmingen) and 80 μg/ml of H-271, CH-271 or CH-296 as described in Example 4. H-271 was coated according to the pre-coating method whereas CH-271 and CH-296 were coated according to the cocktail method.

0.5 ml of Eco-EGFP virus supernatant ($10^7$ cfu/ml) was added to each well of the microplate. The plate was incubated at 32° C. for 3 hours, and then washed with RPMI 1640 medium containing 10% FCS, 50 units/ml of penicillin and 50 μg/ml of streptomycin. $10^5$ CD3-positive T cells derived from mouse spleen cells prepared and pre-stimulated as described in Example 6 were added to the well for viral infection for 3 hours. Thereafter, RPMI 1640 medium containing 10% FCS, 500 units of recombinant mouse interleukin-1α, 10 ng/ml of recombinant mouse interleukin-2, 50 units/ml of penicillin and 50 μg/ml of streptomycin was added to the well. The plate was incubated for additional 48 hours. After incubation, the cells were collected by using a cell detachment buffer, washed and then stained with an anti-mouse CD4 monoclonal antibody (Pharmingen) labeled with phycoerythrin (PE; Pharmingen) and propinium iodide (PI, Sigma). These cells were subjected to flow cytometry using FACSVantage at an excitation wavelength of 488 nm and a emission wavelength of 515–545 nm or 562–588 nm to two-dimensionally analyze CD4 antigen expression and EGFP expression in viable cells. The efficiencies of gene transfer in CD4-positive cells and CD4-negative cells were calculated. The results are shown in Table 12. Table 12 summarizes the results from four rounds of experiments.

TABLE 12

| Functional substance | Efficiency of transfer into CD4-positive cells (%) | Efficiency of transfer into CD4-negative cells (%) |
|---|---|---|
| BSA (control) | 0.16 ± 0.07 | 0.11 ± 0.07 |
| Anti-CD4 antibody | 0.24 ± 0.19 | 0.12 ± 0.04 |
| Anti-CD44 antibody | 1.92 ± 0.82 | 1.95 ± 1.00 |

TABLE 12-continued

| Functional substance | Efficiency of transfer into CD4-positive cells (%) | Efficiency of transfer into CD4-negative cells (%) |
|---|---|---|
| H-271 | 31.02 ± 7.34 | 16.54 ± 4.30 |
| Anti-CD4 antibody/H-271 | 58.91 ± 8.11 | 20.32 ± 4.46 |
| Anti-CD44 antibody/H-271 | 56.08 ± 7.53 | 40.96 ± 7.04 |
| CH-271 | 44.63 ± 6.40 | 26.21 ± 5.73 |
| Anti-CD4 antibody/CH-271 | 64.81 ± 9.74 | 25.97 ± 1.25 |
| Anti-CD44 antibody/CH-271 | 60.29 ± 8.71 | 44.10 ± 3.56 |
| CH-296 | 48.81 ± 8.77 | 29.45 ± 4.70 |
| Anti-CD4 antibody/CH-296 | 62.93 ± 6.45 | 30.84 ± 3.27 |
| Anti-CD44 antibody/CH-296 | 56.79 ± 9.87 | 41.37 ± 1.14 |

(Mean ± standard deviation)

As shown in Table 12, when a retroviral infection was carried out in a plate coated with both of a monoclonal antibody and a fibronectin fragment, an effect of enhancing gene transfer efficiency for CD3-positive T cells derived from mouse spleen cells was observed.

Among others, it should be noted that the efficiency of gene transfer into CD4-positive cells was very higher than that into CD4-negative cells when viral infection was carried out using a combination of an anti-CD4 monoclonal antibody and a functional substance having an activity of binding to a retrovirus. For example, the efficiency of gene transfer into CD4-positive cells using a combination of anti-CD4 monoclonal antibody and H-271 was very high (about 60%), while the efficiency of gene transfer into CD4-negative cells was only about 20%. Similar results were observed when CH-271 or CH-296 was used as a fibronectin fragment.

On the other hand, CD44 antigen is expressed in 98% of more of both CD4-positive cells and CD4-negative cells. Therefore, it was expected that gene transfer efficiency would be increased regardless of the expression of CD4 antigen in the cells when an anti-CD44 monoclonal antibody was used for the retroviral infection as described above. The results in Table 12 confirm such expectation.

Example 9

Gene Transfer Specific for CD8-positive Cells Using Anti-CD8a Monoclonal Antibody Experiments were carried out as described in Example 8 except that H-271 as a functional substance having an activity of binding to a retrovirus, and an anti-mouse CD8a monoclonal antibody (Pharmingen) and an anti-mouse CD44 monoclonal antibody as antibodies were used. An anti-mouse CD8a monoclonal antibody (Pharmingen) labeled with phycoerythrin (PE; Pharmingen) was used for detecting CD8-positive and CDB-negative cells. The results are shown in Table 13. Table 13 summarizes the results from two rounds of experiments.

TABLE 13

| Functional substance | Efficiency of transfer into CD8-positive cells (%) | Efficiency of transfer into CD8-negative cells (%) |
|---|---|---|
| BSA (control) | 0.22 ± 0.08 | 0.28 ± 0.00 |
| Anti-CD8a antibody | 0.36 ± 0.20 | 0.28 ± 0.02 |
| Anti-CD44 antibody | 0.98 ± 0.34 | 0.92 ± 0.20 |

TABLE 13-continued

| Functional substance | Efficiency of transfer into CD8-positive cells (%) | Efficiency of transfer into CD8-negative cells (%) |
|---|---|---|
| H-271 | 20.08 ± 4.71 | 26.43 ± 6.07 |
| Anti-CD8a antibody/H271 | 36.07 ± 1.57 | 24.42 ± 0.55 |
| Anti-CD44 antibody/H271 | 46.93 ± 0.88 | 47.16 ± 0.75 |

(Mean ± standard deviation)

As shown in Table 13, an effect of enhancing the efficiency of gene transfer into CD3-positive T cells derived from mouse spleen cells was observed when the combination of an anti-CD8a monoclonal antibody and a fibronectin fragment was used.

When the anti-CD8a monoclonal antibody was used, as observed in Example 8, high genes transfer efficiency for cells expressing CD8 antigen recognized by the antibody was observed. On the other hand, when a monoclonal antibody against CD44 which is expressed in 98% of more of both CD8-positive cells and CD8-negative cells was used, no difference in gene transfer efficiency was recognized between CD8-positive cells and CD8-negative cells.

The experimental results in Examples 8 and 9 are very significant. These results demonstrate that a gene of interest can be transferred specifically into target cells if a cell population containing target cells is infected with a retrovirus containing the gene of interest in a culture vessel which has been coated using a mixture (cocktail) of an antibody which specifically binds to the target cells and a functional substance having an activity of binding to the virus.

Example 10

Cell-specific Gene Transfer Using an Antibody

A 24-well non-treated microplate for cell culture was coated as described in Example 4 according to the cocktail method using 80 µg/ml of CH-271 and 1 µg/ml of one of monoclonal antibodies against various cell surface antigens (anti-CD4, anti-CD8, anti-CD44, anti-CD49c, anti-CD49d and anti-CD49e antibodies; all from Pharmingen).

K562 (human chronic myelogenous leukemia cell, ATCC CCL-243), HSB-2 (human acute lymphoblastic leukemia cell, CCRF-HSB-2, ATCC CCL-120.1), MOLT-3 (human acute lymphoblastic leukemia cell, ATCC CRL-1552) and TF-1 (human erythroleukemia cell, ATCC CRL-2003) were used as target cells. FACS analysis was carried out on these cells using the labeled respective monoclonal antibodies to determine the expression of antigens corresponding to the antibodies.

0.5 ml of Ampho-EGFP virus supernatant ($1 \times 10^6$ cfu/ml) was added to each well of the microplate. The plate was incubated at 32° C. for 3 hours, and then washed with RPMI 1640 medium containing 10% FCS, 50 units/ml of penicillin and 50 µg/ml of streptomycin. $1 \times 10^5$ of each of the respective cells suspended in 1 ml of the medium was added to the well for viral infection. After incubating for additional 3 days, the cells were collected by using a cell detachment buffer and washed. The efficiency of EGFP gene transfer was calculated according to the flow cytometry method as described in Example 4.

The results are shown Table 14. The mean results from three independent experiments are shown.

TABLE 14

| Antibody used | Cells used | | | | | | | |
|---|---|---|---|---|---|---|---|---|
| | HSB-2 | | MOLT-3 | | TF-1 | | K562 | |
| | Transfer eff. (%) | CD ag exp. ratio | Transfer eff. (%) | CD ag exp. ratio | Transfer eff. (%) | CD ag exp. ratio | Transfer eff. (%) | CD ag exp. rate |
| None | 100 | | 100 | | 100 | | 100 | |
| CD4 | 106.7 | − | 100.7 | +/− | 108.8 | +/− | 104.9 | − |
| CD8 | 130.4 | ++ | 130.4 | ++ | 107.0 | − | 116.9 | − |
| CD44 | 173.7 | ++ | 172.5 | ++ | 188.9 | +++ | 135.1 | − |
| CD49c | 153.9 | +++ | 102.7 | − | 115.6 | − | 106.3 | − |
| CD49d | 159.2 | ++ | 165.3 | +++ | 150.3 | +++ | 97.5 | − |
| CD49e | 185.5 | +++ | 127.5 | + | 128.9 | ++ | 172.6 | +++ |

Gene transfer efficiency (Transfer eff.) is expressed as relative value (%) assuming the efficiency of gene transfer without the addition of an antibody for the respective cells as 100%.

CD antigen expression ratios (CD ag exp. ratio) represent the ratios of positive cells (%) in FACS measurements as follows:

−: 10% or less; +/−: 10–30%; +: 30–60%; ++: 60–90%; +++: 90% or more.

As shown in Table 14, the antigen expression ratio correlated with the efficiency of gene transfer using the cocktail method in which CH-271 as a virus-binding substance and the antibody against the antigen on the cell as a cell-binding substance were used.

Furthermore, gene transfer experiments were carried out using 80 μg/ml of polylysine as a functional substance having an activity of binding to a retrovirus in place of CH-271. Monoclonal antibodies and cells used as well as other experimental conditions were as described above. The results are shown in Table 15. The mean results from three independent experiments are shown.

cocktail method in which polylysine as a virus-binding substance and the antibody against the antigen on the cell as a cell-binding substance were used.

The two series of experimental results as described above demonstrate that a gene can be transferred specifically into target cells of interest by transferring a gene according to the cocktail method using an antibody that specifically recognizes an antigen expressed on the target cell as a cell-binding substance.

Example 11

Gene Transfer Into Target Cells Pre-cultured in Medium Containing Deferoxamine

Human myelocytic leukemia HL-60 cells (ATCC CCL-240) cultured in RPMI 1640 medium containing 10% FCS, 50 units/ml of penicillin and 50 μg/ml of streptomycin were transferred into the same medium containing deferoxamine (Sigma) at a varying concentration on the day before the infection experiments. The cells were cultured at 37° C. for 20 hours in the presence of 5% $CO_2$. The cells were washed

TABLE 15

| Antibody used | Cells used | | | | | | | |
|---|---|---|---|---|---|---|---|---|
| | HSB-2 | | MOLT-3 | | TF-1 | | K562 | |
| | Transfer eff. (%) | CD ag exp. ratio | Transfer eff. (%) | CD ag exp. ratio | Transfer eff. (%) | CD ag exp. ratio | Transfer eff. (%) | CD ag exp. rate |
| None | 100 | | 100 | | 100 | | 100 | |
| CD4 | 103.3 | − | 104.1 | +/− | 98.6 | +/− | 99.4 | − |
| CD8 | 116.3 | ++ | 136.7 | ++ | 100.8 | − | 92.4 | − |
| CD44 | 155.5 | ++ | 144.9 | ++ | 253.1 | +++ | 102.6 | − |
| CD49c | 160.1 | +++ | 104.7 | − | 116.1 | − | 100.6 | − |
| CD49d | 138.2 | ++ | 156.3 | +++ | 187.7 | +++ | 103.1 | − |
| CD49e | 142.5 | +++ | 140.0 | + | 166.1 | ++ | 129.2 | +++ |

Gene transfer efficiency (Transfer eff.) is expressed as relative value (%) assuming the efficiency of gene transfer without the addition of an antibody for the respective cells as 100%.

CD antigen expression ratios (CD ag exp. ratio) represent the ratios of positive cells (%) in FACS measurements as follows:

−: 10% or less; +/−: 10–30%; +: 30–60%; ++: 60–90%; +++: 90% or more.

As shown in Table 15, the antigen expression ratio correlated with the efficiency of gene transfers using the with fresh medium without deferoxamine upon use, and then suspended at a concentration of $2 \times 10^5$ cells/ml for use in the following infection experiments.

0.5 ml of 80 μg/ml CH-271 was added to each well of a 24-well non-treated microplate for cell culture. The plate was allowed to stand at 4° C. overnight, blocked using 2% BSA for 30 minutes and washed with PBS. 0.5 ml of Ampho-EGFP virus supernatant ($10^6$ cfu/ml) was added to the well of the microplate. The plate was incubated at 32° C. for 3 hours and washed with RPMI 1640 medium containing 10% FCS, 50 units/ml of penicillin and 50 μg/ml of streptomycin. $10^5$ of the pre-cultured HL-60 cells were added to the well. The plate was incubated for 48 hours. 0.5 ml of RPMI 1640 medium containing 10% FCS, 50 units/ml of penicillin and 50 μg/ml of streptomycin was added to the well. The plate was incubated for additional 24 hours. Thereafter, the gene transfer efficiency was determined as described in Example 4. The results are shown in Tables 16 and 17.

TABLE 16

| Deferoxamine concentration (μg) | Functional substance | Transfer efficiency (%) |
| --- | --- | --- |
| No addition | BSA (control) | 0.01 |
| No addition | CH-271 | 0.14 |
| 6.25 | CH-271 | 0.22 |
| 12.5 | CH-271 | 0.27 |
| 25 | CH-271 | 0.35 |
| 50 | CH-271 | 0.71 |

TABLE 17

| Deferoxamine concentration (μg) | Functional substance | Transfer efficiency (%) |
| --- | --- | --- |
| No addition | BSA (control) | 0.02 |
| No addition | CH-271 | 0.25 |
| 40 | CH-271 | 11.14 |

As shown in Tables 16 and 17, increase in gene transfer efficiency was observed even for HL-60 cells by pre-treating the cells with deferoxamine for 20 hours. It was known that a gene is transferred into HL-60 cells with very low efficiency using CH-271 alone.

Example 12

Detection of Presence of Viral Infection-inhibitory Substances in Culture Supernatant The TKNeo virus supernatant prepared in Example 2 was diluted with DMEM, a culture supernatant of NIH/3T3 cells (ATCC CRL-1658) or a culture supernatant of SCRIP cells to a concentration of 312.5 cfu/ml for use in the following procedures.

0.5 ml of 32 μg/ml CH-296 was added to each well of a 24-well non-treated microplate for cell culture. The plate was allowed to stand at room temperature for 2 hours, blocked with 2% BSA for 30 minutes and washed with PBS. 1 ml of the above-mentioned virus supernatant and $2 \times 10^4$ NIH/3T3 cells were added to the well of the plate. The plate was incubated at 37° C. overnight. The cells were then cultured in a selective medium containing 0.75 mg/ml of G418 for 10 days. The number of colonies formed was counted. The ratio of the number of G418-resistant colonies to the number of colonies formed in a medium without G418 was defined as gene transfer efficiency. The results are shown in Table 18.

TABLE 18

| Diluent | Gene transfer efficiency (%) |
| --- | --- |
| DMEM (control) | 100 |
| NIH/3T3 cell | 20.6 |

TABLE 18-continued

| Diluent | Gene transfer efficiency (%) |
| --- | --- |
| culture supernatant φCRIP cell culture supernatant | 15.7 |

As shown in Table 18, the gene transfer efficiencies were decreased to one fifth or less when the dilution of virus with the culture supernatant of NIH/3T3 cells or the culture supernatant of φCRIP cells was used as compared with the efficiency of gene transfer using the dilution with DMEM. NIH/3T3 cell is the parent strain of many packaging cell lines such as φCRIP cell and GP+EmvAm12 cell, which was used to generate the producer cell for the TKNeo virus vector used in this experiment. The fact that an activity of inhibiting retroviral infection was found in the culture supernatants of these cells suggests that virus supernatants prepared using similar packaging cells also contain inhibitory substances.

Example 13

Removal of Viral Infection-inhibitory Substance in Virus Supernatant

The following procedures were used to remove the viral infection-inhibitory substance found in Example 12. The TKNeo virus supernatant prepared in Example 2 was diluted with the culture supernatant of φCRIP cells to a concentration of 5000 cfu/ml. The diluted supernatant was further doubly diluted with DMEM for use as a sample containing a retrovirus.

1 ml of the virus supernatant was added to each well of a plate coated with CH-296 as described in Example 11. The plate was incubated for 1 to 5 hours for contacting and binding the virus particles with CH-296. The plate was then washed three times with PBS. 1 ml of DMEM containing $2 \times 10^4$ NIH/3T3 cells was added to the well. As a control, $2 \times 10^4$ NIH/3T3 cells were suspended in 1 ml of the above-mentioned virus supernatant and then immediately transferred to the plate coated with CH-296. These plates were incubated at 37° C. overnight to allow the virus to infect cells. After infection, the cells were cultured in a selective medium containing 0.75 mg/ml of G418 for 10 days, and the number of colonies formed were counted. The ratio of the number of G418-resistant colonies to the number of colonies formed in a medium without G418 was defined as gene transfer efficiency. The results are shown in FIG. 3.

Figure 3:
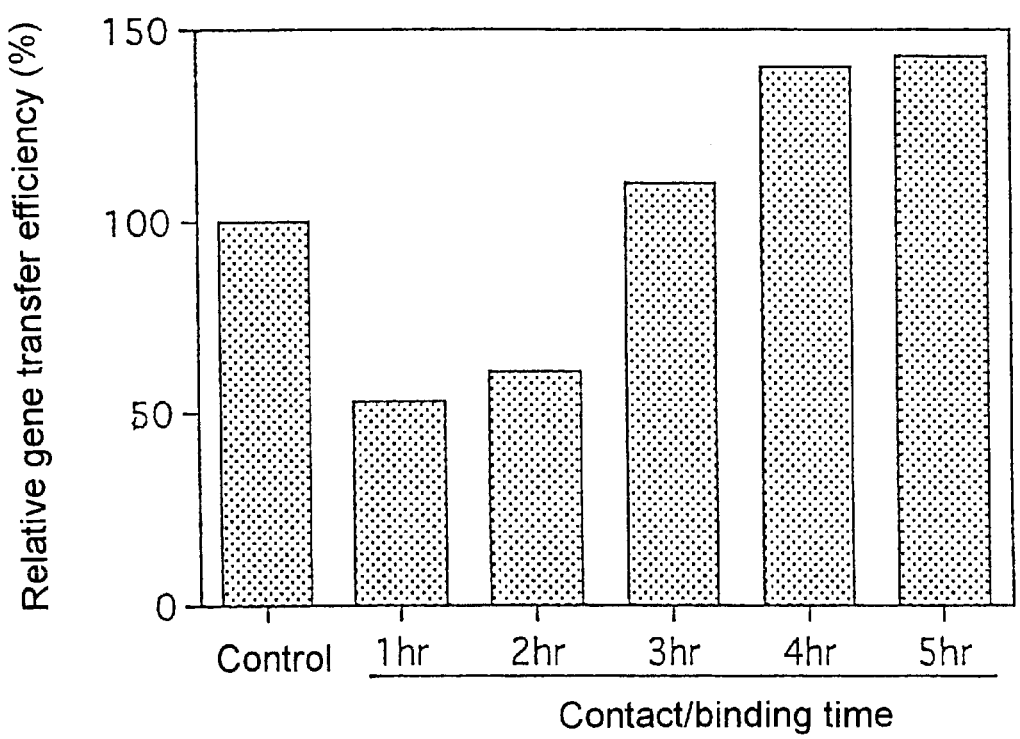
FIG. 3 is a graph that shows the relationship between relative gene transfer efficiency (%) and contact/binding time in a study on effect of removing viral infection-inhibitory substances in Example 13.

As shown in FIG. 3, higher transfer efficiency was observed at 3 hours when virus particles were contacted with and bound to the CH-296 coated plate as compared with the efficiency for the control group. Thus, it was demonstrated that the activity of inhibiting viral infection in a virus supernatant could be removed by the procedures as described above.

Example 14

Removal of Sodium Butyrate in Virus Supernatant

Recombinant retrovirus-producer cells obtained by introducing a retrovirus vector plasmid pLEIN into φCRIP cells were cultured in DMEM containing 10% CS. When the cells grew to semi-confluence in a 10-cm plate, the medium was changed to 7 ml of RPMI 1640 containing 10% FCS or 7 ml of RPMI 1640 containing 5 mM sodium butyrate (Nacalai Tesque) and 10% FCS. After the cells were cultured for 24 hours, supernatants were filtered through 0.45 μm filters to obtain virus supernatants. The titer of the virus supernatant was determined as described in Example 2. The titer of the virus supernatant without sodium butyrate was $3.3 \times 10^4$ cfu/ml, whereas the titer of the virus supernatant containing 5 mM sodium butyrate was $2 \times 10^6$ cfu/ml.

Sodium butyrate has activities of arresting cell cycle to suppress cell growth and inducing differentiation. Thus, it may have harmful influence on infected cells. Removal of sodium butyrate contained in a virus supernatant was assessed as follows.

HL-60 cells were used as target cells. 0.5 ml of the above-mentioned virus supernatant was added to each well of a plate coated with CH-296 as described in Example 12. The plate was incubated at 37° C. for 3 hours for contacting and binding the virus particles with CH-296. After incubation, the plate was washed three times with PBS. 0.5 ml of RPMI 1640 medium supplemented with 10% FCS containing $5 \times 10^4$ HL-60 cells was added to the well. As a control, $5 \times 10^4$ HL-60 cells were suspended in 0.5 ml of the above-mentioned virus supernatant and then immediately added to the plate coated with CH-296. These plates were incubated at 37° C. overnight to allow the virus to infect cells. After the incubation, 1 ml of RPMI 1640 medium containing 10% FCS was added to the well. The plate was incubated for additional 48 hours. The cell number was then counted. Furthermore, EGFP-expressing cells were detected according to the flow cytometry method as described in Example 4 to analyze the gene transfer efficiency. The results are shown in Table 19.

TABLE 19

| Experimental group/<br>virus supernatant | Cell number<br>(cells/plate) | Gene transfer<br>efficiency (%) |
|---|---|---|
| CH-296 | | |
| Sodium butyrate: − | $2.0 \times 10^5$ | 2.21 |
| Sodium butyrate: + | $1.8 \times 10^5$ | 52.98 |
| Control | | |
| Sodium butyrate: − | $1.7 \times 10^5$ | 2.74 |
| Sodium butyrate: + | $4.0 \times 10^5$ | 35.46 |

As shown in Table 19, higher gene transfer efficiency was observed for the control group when a virus supernatant prepared by adding sodium butyrate was used, confirming the effectiveness of sodium butyrate in virus preparation. However, the viable cell number observed using the supernatant containing sodium butyrate was one fourth or less of that observed using the supernatant without sodium butyrate, confirming that sodium butyrate suppressed cell growth. On the other hand, when the virus particles were contacted with and bound to the CH-296 coated plate beforehand, the cell growth suppression, which was observed for control group using the supernatant containing sodium butyrate, was not observed. Increase, rather than decrease, in gene transfer efficiency was observed. Thus, it was demonstrated that high gene transfer efficiency could be accomplished without the influence of sodium butyrate by contacting virus with CH-296 followed by washing.

Next, DEAE-dextran was used to carry out similar experiments.

DEAE-dextran (Sigma) was dissolved at a concentration of 10 mg/ml in PBS. The solution was sterilized by filtering through a 0.22 μm filter and used to coat a plate. 1.1 ml of a mixture obtained by mixing 10 volumes of PBS and 1 volume of the DEAE-dextran solution was added to each well of a 6-well non-treated plate for cell culture (Iwaki Glass). The plate was incubated at 4° C. overnight. The DEAE-dextran solution was removed from the plate. 2 ml of 2% BSA solution was added to the well for treatment for 30 minutes. The plate was washed three times with 2 ml/well of PBS. As a control, a plate was prepared by conducting the same procedures except that PBS was used in place of the DEAE-dextran solution.

A virus supernatant was prepared according to the method in which sodium butyrate was added as described above using recombinant retrovirus-producer cells produced by introducing a retrovirus vector plasmid PLEIN into GP+E86 cells [J. Virol., 62:1120–1124 (1988)]. 1 ml of a virus dilution ($1.6 \times 10^6$ cfu/ml) obtained by diluting 1 volume of the virus supernatant with 20 volumes of DMEM containing 10% CS was added to each well. The plate was incubated at 37° C. for 2 hours, and then washed three times with 2 ml/well of PBS. $5 \times 10^4$ NIH/3T3 cells were added to the well. The plate was incubated at 37° C. for 3 days in the presence of 5% $CO_2$. After incubation, the cells were treated with trypsin and collected. EGFP-expressing cells were analyzed according to the flow cytometry method as described in Example 4 to determine the gene transfer efficiency. The results are shown in Table 20.

TABLE 20

| Coating | Gene transfer efficiency (%) |
|---|---|
| DEAE-dextran | 26.7 |
| Control | 0.7 |

Gene transfer efficiency represented by the ratio (%) of EGFP-positive cells to total cells is indicated.

As shown in Table 20, it was demonstrated that DEAE-dextran also has an activity of binding to a retrovirus, and it can be used for the gene transfer method of the present invention.

Example 15

Binding of Functional Substance to Retrovirus Utilizing Centrifugation Method

φCRIP cells into which a retrovirus plasmid, DOL vector, containing a neomycin-resistance gene [Proc. Natl. Acad. Sci. USA, 84:2150–2154 (1987)] had been introduced were cultured in DMEM containing 10% CS, 50 units/ml of penicillin and 50 μ/ml of streptomycin. A DOL virus supernatant was prepared as follows. Medium in a 10-cm plate in which the producer cells had grown to semi-confluence was changed to 5 ml of DMEM containing 10% CS. After 24 hours, the supernatant was collected and filtered through a 0.45 μm filter (Millipore). The titer of the virus supernatant was $8.7 \times 10^5$ cfu/ml.

A centrifugation tube (50 ml polypropylene conical tube, Falcon) used for infecting cells with a retrovirus was coated with CH-296 as follows. Briefly, 3 ml of PBS containing 40 μ/ml of CH-296 was slowly placed to the bottom of the centrifugation tube. The tube was allowed to stand upright for incubation at 4° C. for 16 hours. The CH-296 solution was exchanged for 3.5 ml of PBS containing 2% BSA. The tube was incubated for additional 30 minutes at room temperature, and then washed with 5 ml of Hanks' balanced salt solution (HBSS, Gibco).

The DOL retrovirus was bound to the bottom of the centrifugation tube coated with CH-296 as follows. Briefly, 5 ml of the undiluted DOL virus supernatant, or a 10-fold or 100-fold dilution thereof was placed in the centrifugation tube. The tube was centrifuged at 2900×g at 25° C. for 3 hours to force the retrovirus to bind to CH-296. For comparison, the above-mentioned virus supernatant was added to a 6-well non-treated plate for cell culture (Falcon) coated with CH-296 using PBS containing 40 μg/ml of CH-296 so as to result in a density of 8 μg/cm$^2$. The plate was allowed to stand at 37° C. for 4 hours for binding and used in the following procedures.

Figure 4:
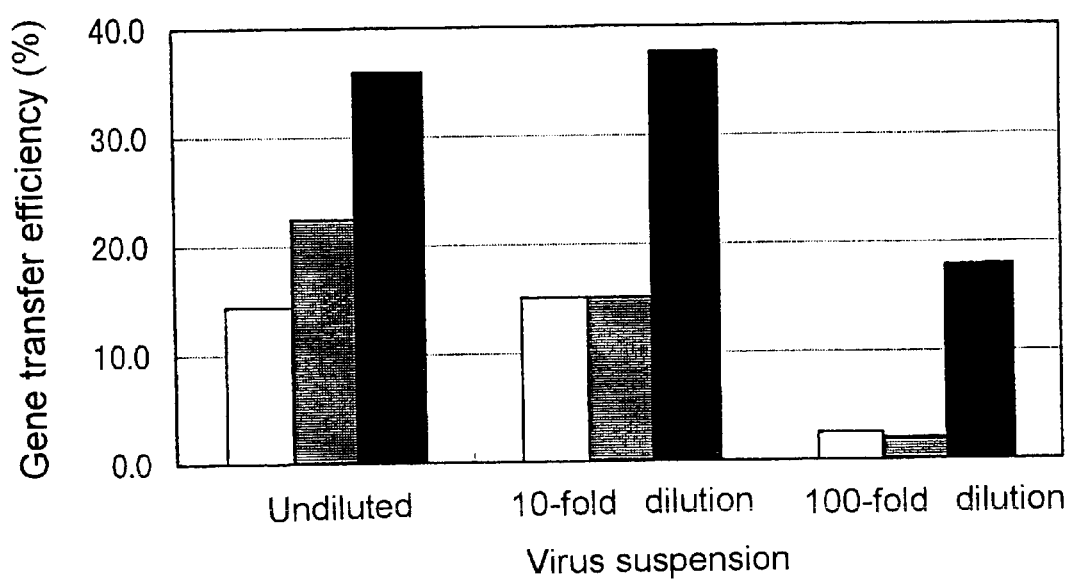
FIG. 4 is a graph which shows the relationship between relative gene transfer efficiency (%) and respective virus-binding procedures in a study on effect of binding retroviruses to functional substances utilizing the centrifugation method in Example 15.

Gene transfer into NIH/3T3 cells was carried out using the centrifugation tube coated with CH-296 to which the retrovirus had been forced to bind by centrifugation. Briefly, 1×10$^5$ NIH/3T3 cells were placed in the centrifugation tube coated with CH-296 in which one of the serial dilutions of the virus supernatant had been centrifuged. The tube was incubated at 37° C. for 3 hours (hereinafter referred to as the centrifugation method) Alternatively, the above-mentioned microplate was incubated under the same conditions (hereinafter referred to as the binding method). As a control, a mixture of the virus supernatant and NIH/3T3 cells was added to the microplate coated with CH-296, and the plate was incubated at 37° C. for 3 hours. The results obtained using the last method were defined as those of a conventional infection method and used for comparison (hereinafter referred to as the supernatant method). After incubation, the cells were collected. The efficiency of gene transfer in the collected cells was determined as described in Example 13. The results are shown in FIG. 4. In FIG. 4, the horizontal axis represents the dilution rate of the virus supernatant and the vertical axis represents the gene transfer efficiency. The open bars, shaded bars and closed bars represent results obtained using the supernatant method, the binding method and the centrifugation method, respectively.

As shown in FIG. 4, the efficiency of gene transfer using the centrifugation method was higher than that using the conventional supernatant method and the method in which the virus had been spontaneously adsorbed to CH-296 prior to the infection (the binding method) Thus, it was demonstrated that more virus particles bound to CH-296 at the bottom of the vessel by forcing the virus to precipitate by centrifugal force. In particular, the effect due to the centrifugation was remarkable when a diluted virus supernatant was used.

Furthermore, the titers of the virus supernatants collected after the binding of virus using centrifugation or standing (binding) were measured. The results are shown in Table 21.

TABLE 21

| Sample | Virus titer (cfu/ml) | Recovery after binding (%) |
|---|---|---|
| Virus supernatant (before use) | 8.7 x 10$^5$ | 100 |
| Collected supernatant - binding method | 7.8 x 10$^5$ | 89.4 |
| Collected supernatant - centrifugation method | 7.6 x 10$^4$ | 8.8 |

As shown in Table 21, in the case of standing, the collected supernatant had about 80 to 90% of the titer of the supernatant before binding. On the other hand, the titer of the supernatant after forcing to bind by centrifugation was one tenth or less of that of the supernatant before binding. These results demonstrate that more virus particles were bound to CH-296 by centrifugal force. PBS used to wash the centrifugation tube after centrifugation contained about 2% of the original amount of the virus. In addition, almost the same gene transfer efficiency was observed regardless of the presence of the washing step. These results suggest that the virus particles were firmly held by CH-296 when centrifugation was utilized.

Furthermore, the efficiency of gene transfer by the centrifugation method was compared with that by a method in which cells are infected with a virus during centrifugation.

The efficiency of gene transfer into NIH/3T3 cells by the centrifugation method was compared with that by the centrifugation-infection method, in which a virus is precipitated by centrifugal force onto cells for infection (see WO 95/10619). 5 ml of a virus supernatant prepared by diluting the virus supernatant prepared using GP+E86 cells as described in Example 14 with a culture supernatant of NIH/3T3 cells to a concentration of 1×10$^5$ cfu/ml was used for the comparison. Briefly, gene transfer was carried out as follows. The above-mentioned virus supernatant was added to a centrifugation tube coated with CH-296. The tube was centrifuged at 30° C. at 2900×g for 4 hours, and then washed with PBS. Cells were then added to the tube for infection at 37° C. for 4 hours (the centrifugation method). Cell were added to a centrifugation tube coated with CH-296, and cultured for 2 hours. The virus supernatant was added to the tube. The tube was centrifuged at 30° C. at 2900×g for 4 hours for infection (the centrifugation-infection method). In these methods, the centrifugation tubes were coated with CH-296 as described above, and 1×10$^5$ NIH/3T3 cells were used for gene transfer. The cells after infection were re-plated into a 60-mm plate, and cultured for 2 days. The efficiency of the EGFP gene transfer was then determined according to the flow cytometry method as described in Example 4. The results are shown in FIG. 5.

Figure 5:
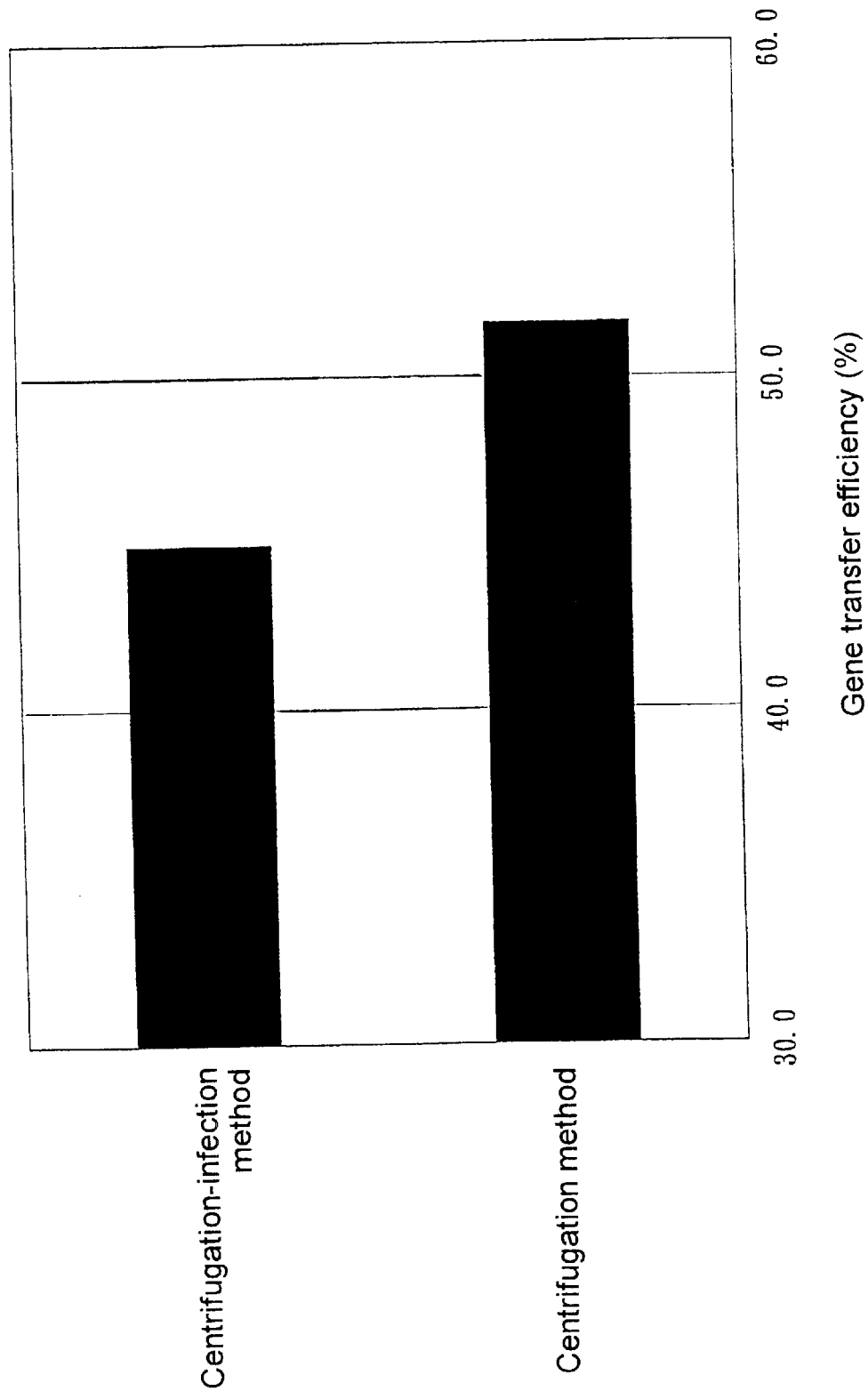
FIG. 5 is a graph that shows gene transfer efficiency (%) achieved by using the centrifugation method or the centrifugation-infection method in Example 15.

As shown in FIG. 5, it was demonstrated that the efficiency of gene transfer by the centrifugation method was higher than that by the centrifugation-infection method. It is considered that this is because infection-inhibitory substance in the virus supernatant was removed by washing.

What is claimed is:

1. A method for transferring a gene into target cells using a retrovirus, comprising:

(1) contacting a solution containing a retrovirus with a functional substance that binds to the retrovirus and is immobilized on a substrate for 3 hours or longer;

(2) washing the substrate to which the retrovirus is bound; and (3) contacting and incubating the substance to which the retrovirus is bound with target cells.

2. The method according to claim 1, wherein step (1) is carried out by precipitating the retrovirus by centrifugal force onto the functional substance that binds to the retrovirus and being immobilized on the substrate.

3. The method according to claim 1, wherein the functional substance that binds to the retrovirus is selected from the group consisting of fibronectin, fibroblast growth factor, collagen type V, polylysine and DEAE-dextran, as well as fragments thereof.

4. The method according to claim 1, wherein the functional substance that binds to the retrovirus binds to target cells.

5. The method according to 1, wherein a substrate is used on which the functional substance that binds to the retrovirus and another functional substance that binds to the target cells are immobilized.

6. The method according to claim 1, wherein a vessel for cell culture or a particulate substrate is used as the substrate.

7. The method according to claim 1, wherein the solution containing the retrovirus is a culture supernatant of retrovirus-producer cells obtained in the presence of a substance that enhances retrovirus production.

8. A method for transferring a gene into target cells using a retrovirus, comprising:
   (1) contacting a solution containing a retrovirus with a functional substance that binds to the retrovirus and being immobilized on a substrate;
   (2) washing the substrate to which the retrovirus is bound; and
   (3) contacting and incubating the substrate to which the retrovirus is bound with target cells, wherein the frequency of contact between the retrovirus and the functional substance having an activity of binding to the retrovirus is physically increased in step (1).

9. The method according to claim 5, wherein the functional substance that binds to the target cells is selected from the group consisting of cell-adhesive proteins, hormones, cytokines, antibodies, sugar chains, carbohydrates and metabolites.

10. The method according to claim 7, wherein the solution containing the retrovirus is a culture supernatant obtained in the presence of sodium butyrate.

11. The method according to claim 8, wherein step (1) is carried out by precipitating the retrovirus by centrifugal force onto the functional substance having an activity of binding to the retrovirus and being immobilized on the substrate.

12. The method according to claim 8, wherein the functional substance that binds to the retrovirus is selected from the group consisting of fibronectin, fibroblast growth factor, collagen type V, polylysine and DEAE-dextran, as well as fragments thereof.

13. The method according to claim 8, wherein the functional substance that binds to the retrovirus binds to target cells.

14. The method according to claim 8, wherein a substrate is used on which the functional substance that binds to the retrovirus and another functional substance that binds to the target cells are immobilized.

15. The method according to claim 8, wherein a vessel for cell culture or a particulate substrate is used as the substrate.

16. The method according to claim 8, wherein the solution containing the retrovirus is a culture supernatant of retrovirus-producer cells obtained in the presence of a substance that enhances retrovirus production.

17. A method for transferring a gene into target cells using a retrovirus, characterized in that the method comprises infecting target cells with a retrovirus in the presence of two functional substances:
   (1) a functional substance having an activity of binding to the retrovirus; and
   (2) an antibody which specifically binds to a CD antigen expressed on the target cells.

18. The method according to claim 17, wherein the functional substance that binds to the retrovirus is selected from the group consisting of fibronectin, fibroblast growth factor, collagen type V, polylysine and DEAE-dextran, as well as fragments thereof.

19. The method according to claim 17, wherein at least one of the two functional substances is immobilized on a substrate.

20. A method for transferring a gene into target cells using a retrovirus, characterized in that the method comprises infecting target cells with a retrovirus in the presence of two functional substances:
   (1) a functional substance that binds to the retrovirus; and
   (2) a sugar chain derived from laminin or a high mannose type sugar chain.

21. The method according to claim 18, wherein the functional substance that binds to the retrovirus has an activity of binding to target cells.

22. The method according to claim 19, wherein a vessel for cell culture or a particulate substrate is used as the substrate.

23. The method according to claim 20, wherein the functional substance that binds to the retrovirus is selected from the group consisting of fibronectin, fibroblast growth factor, collagen type V, polylysine and DEAE-dextran, as well as fragments thereof.

24. The method according to claim 20, wherein at least one of the two functional substances is immobilized on a substrate.

25. The method according to claim 20, wherein the functional substance that binds to the retrovirus is selected from the group consisting of fibronectin, fibroblast growth factor, collagen type V, polylysine and DEAE-dextran, as well as fragments thereof.

26. The method according to claim 20, wherein at least one of the two functional substances is immobilized on a substrate.

* * * * *